US010041855B2

(12) United States Patent
Nino et al.

(10) Patent No.: US 10,041,855 B2
(45) Date of Patent: Aug. 7, 2018

(54) FUSE-LIKE SENSOR, DETECTION AND MEASUREMENT SYSTEMS

(71) Applicant: Quest Integrated, Inc., Kent, WA (US)

(72) Inventors: Giovanni Nino, Issaquah, WA (US); Tyler Blumenthal, Renton, WA (US)

(73) Assignee: QUEST INTEGRATED, INC., Kent, WA (US)

( * ) Notice: Subject to any disclaimer, the term of this patent is extended or adjusted under 35 U.S.C. 154(b) by 0 days.

(21) Appl. No.: 14/602,195

(22) Filed: Jan. 21, 2015

(65) Prior Publication Data

US 2015/0226579 A1 Aug. 13, 2015

Related U.S. Application Data

(60) Provisional application No. 61/929,902, filed on Jan. 21, 2014.

(51) Int. Cl.
G01B 7/16 (2006.01)
G01L 1/00 (2006.01)
G01M 5/00 (2006.01)
G01N 19/08 (2006.01)
H05K 1/02 (2006.01)
G01N 27/20 (2006.01)
H05K 1/16 (2006.01)
G01N 27/24 (2006.01)

(52) U.S. Cl.
CPC ........ G01M 5/0033 (2013.01); G01M 5/0083 (2013.01); G01N 19/08 (2013.01); G01N 27/205 (2013.01); H05K 1/0293 (2013.01); G01N 27/24 (2013.01); H05K 1/16 (2013.01); H05K 2201/10151 (2013.01)

(58) Field of Classification Search
CPC ............ G01D 5/12; G01D 5/24; G01N 19/08; G01M 5/0033; G01M 5/0083; H05K 1/0293
USPC .................................. 73/774, 775; 324/537
See application file for complete search history.

(56) References Cited

U.S. PATENT DOCUMENTS

| 3,803,485 A | * | 4/1974 | Crites et al. ......... | G01N 27/205 324/693 |
| 4,255,974 A | * | 3/1981 | Dufrane et al. ......... | G01B 7/18 73/776 |
| 4,484,132 A | * | 11/1984 | Crites .................. | G01N 27/205 324/557 |

(Continued)

OTHER PUBLICATIONS

Author: Mathew P. Kotowsky, Title: Wireless Sensor Networks for Monitoring Cracks in Structures, Date: Jun. 2010, Publisher: NorthWestern University, pp. 184.*
Authors: Jibendu Sekhar Roy, Dipak Ranjan Poddar, Amitava Mukherjee, and Santosh Kumar Chowdhury, Title: Dispersion Characteristics of Curved Microstrip Transmission Lines, Date: Aug. 1990, Publisher: IEEE Transactions on Microwave Theory and Technioues, vol. 38, No. 8, pp. 1366-1370.*
International Search Report and Written Opinion dated May 4, 2015, issued in corresponding International Application No. PCT/US2015/012312, filed Jan. 21, 2015, 12 pages.
Farrar, C.R., and K. Worden, "An Introduction to Structural Health Monitoring," Philosophical Transactions of the Royal Society, 365:303-315, Dec. 2006.
Hon, K.K.B., et al., "Direct Writing Technology—Advances and Developments," CIRP Annals—Manufacturing Technology, 57(2):601-620, Dec. 2008.

(Continued)

Primary Examiner — Lisa Caputo
Assistant Examiner — Roger Hernandez-Prewit
(74) Attorney, Agent, or Firm — Christensen O'Connor Johnson Kindness PLLC

(57) ABSTRACT

A system includes a substrate having a surface and a circuit with a plurality of conductive paths disposed adjacent (e.g., directly on or separated by a thin layer). The circuit is configured to detect an interruption or alteration of conduction of one or more of the plurality of conductive paths due to a flaw in the substrate. The circuit is further configured to identify the interrupted or altered one or more of the plurality of conductive paths based on one or more electrical characteristics of the circuit.

18 Claims, 19 Drawing Sheets

(56) References Cited

U.S. PATENT DOCUMENTS

| | | | |
|---|---|---|---|
| 4,895,735 A * | 1/1990 | Cook | C23C 14/048 |
| | | | 156/234 |
| 5,017,509 A * | 5/1991 | Tuckerman | H01P 11/003 |
| | | | 438/622 |
| 5,936,411 A * | 8/1999 | Jacobsen et al. | G01B 7/16 |
| | | | 324/662 |
| 8,617,965 B1 * | 12/2013 | Quick et al. | H01L 21/02381 |
| | | | 438/478 |
| 2005/0200493 A1 | 9/2005 | Marishak, Jr. | |
| 2005/0223812 A1 | 10/2005 | Denis | |
| 2009/0007686 A1 | 1/2009 | Sumigawa et al. | |
| 2009/0007687 A1 | 1/2009 | Arms et al. | |
| 2009/0007688 A1 | 1/2009 | Foote | |
| 2010/0094566 A1 * | 4/2010 | Grant et al. | G01M 5/0016 |
| | | | 702/38 |
| 2011/0095772 A1 | 4/2011 | Sidhu et al. | |
| 2011/0207328 A1 * | 8/2011 | Speakman | H01L 51/0016 |
| | | | 438/694 |
| 2012/0060621 A1 | 3/2012 | Ozkul et al. | |
| 2012/0197482 A1 | 8/2012 | Moser et al. | |
| 2012/0273263 A1 * | 11/2012 | Nagarajan et al. | H05K 1/097 |
| | | | 174/257 |

OTHER PUBLICATIONS

Lacivita, K.J., "Informal Evaluation of Vacuum-Based Crack Detection Sensor (Equipment Evaluation)," Air Force Research Laboratory/Systems Support Division (AFRL/MLS) Report No. AFRL/MLS 01-076, Sep. 2001, 19 pages.

Roach, D., et al., "Use of Composite Materials, Health Monitoring and Self-Healing Concepts to Refurbish Our Civil and Military Infrastructure," SANDIA National Laboratories, Report No. SAND2007-5547, Sep. 2007, 400 pages.

Stehmeier, H., and H. Speckmann, "Comparative Vacuum Monitoring (CVM)—Monitoring of Fatigue Cracking in Aircraft Structures," Proceedings of the 2nd European Workshop on Structural Health Monitoring, Munich, Jul. 2004, 8 pages.

* cited by examiner

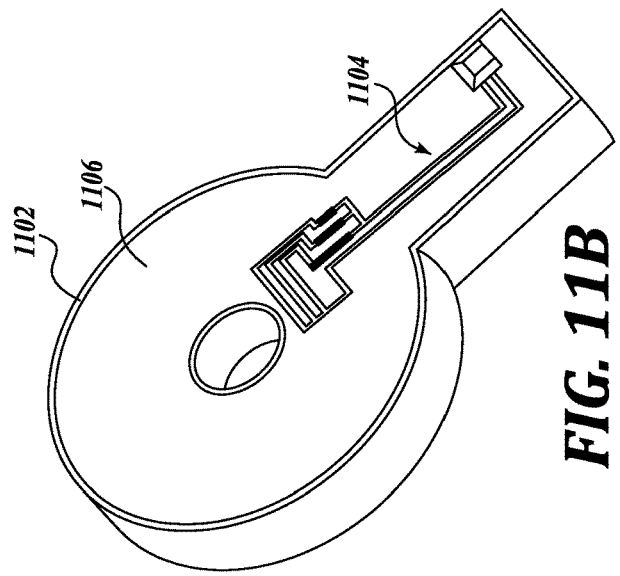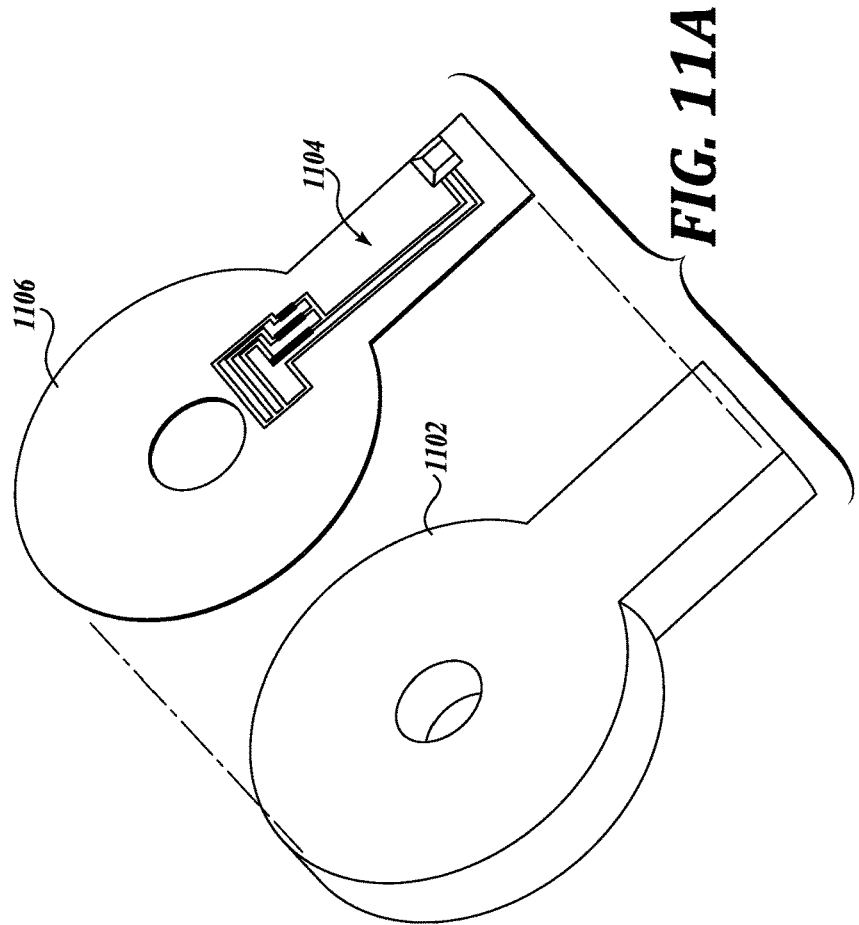

FUSE-LIKE SENSOR, DETECTION AND MEASUREMENT SYSTEMS

CROSS-REFERENCE TO RELATED APPLICATION

This application claims the benefit of U.S. Provisional Patent Application No. 61/929,902, filed Jan. 21, 2014, the disclosure of which is hereby incorporated by reference in its entirety.

FIELD OF DISCLOSED SUBJECT MATTER

The subject matter disclosed herein pertains generally to sensors for structural monitoring. More specifically, the subject matter relates to a sensor with fuses for flaw or event indication that has been deposited or transferred onto a host structure using additive manufacturing techniques for electronics fabrication. Sensors may include an array of fuses that change their physical or chemical condition under damage or an unexpected event. The sensors may include a connector for establishing electrical or magnetic communication with an external interrogation instrument.

BACKGROUND

With the increased usage of modern structures and structural systems, industry is faced with even more demands to understand performance during usage and durability over time. This situation occurs on metallic, composite and ceramic structures where the presence of damages could affect their structural integrity. This situation also occurs where changes in chemical atmosphere or surrounding environment due to leakages are critical for the performance of a system or for the health of personnel or ecosystem. In many cases, highly stressed areas or "hot spots" occur on zones with limited access or no access at all. These hot spots can be found on structural elements that transfer load from one sub-structure system into another. For example, in aircraft, hot spots are frequently found on structural interface members such as landing gear/wing, landing gear/fuselage, wing/fuselage, engine pylon/fuselage, and bulkheads/fuselage among others. Some of those structures are critical and may hide serious damage. Current Non Destructive Inspection (NDI) methods detect and monitor damage when a structure is undergoing routine maintenance. However, inspecting assembled structures is difficult and sometimes impossible due to hardware assembly and/or limited access. In addition, conventional inspections of these spots may require time consuming and expensive disassembly tasks.

Thanks to the advance of embedded systems, additive manufacturing, and signal processing, there is a transition from conventional NDI methods into Structural Health Monitoring (SHM) methods. Placing sensors on the structures has been around for more than 30 years and it has demonstrated feasibility in laboratory and controlled testing environments on aerospace, mechanical engineering, and civil infrastructure applications. See Farrar C., and Worden, K., "An Introduction to Structural Health Monitoring," Phil. Trans. R. Soc. A (2007), 365. In general, SHM consists of a set of sensors and actuators embedded into a given system or bonded onto one of its surfaces such as plates, blades, or panels, plus electronics for interrogation, data acquisition, and processing. It is important to mention that conventional sensors do not measure any damage, they only sense the structure response to a given excitation signal or change in environmental conditions. Thus, differences between responses measured at different times or above some given threshold may indicate the presence of damage or a change of physical or chemical state.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, a system is provided. In one embodiment, the system includes:
 a substrate having a surface; and
 a circuit including a plurality of conductive paths disposed adjacent the surface of the substrate, wherein the circuit is configured to:
  detect an interruption or alteration of conduction of one or more of the plurality of conductive paths due to a flaw in the substrate, and
  identify the interrupted or altered one or more of the plurality of conductive paths based on one or more electrical characteristics of the circuit.

In another aspect, a system is provided. In one embodiment, the system includes:
 a substrate having a surface;
 a transferable medium; and
 a circuit including a plurality of conductive paths disposed adjacent the transferable medium, wherein the transferable medium is bonded to the surface of the substrate such that the circuit is configured to:
  detect an interruption or alteration of conduction of one or more of the plurality of conductive paths due to a flaw in the substrate, and
  identify the interrupted or altered one or more of the plurality of conductive paths based on one or more electrical characteristics of the circuit.

In one aspect, a method of producing a structural health monitoring crack detection system is provided. In one embodiment, the method includes:
 providing a substrate having a surface; and
 printing, by an aerosol jet method, conductive paths on the surface of the substrate, wherein the resistive traces are configured to break if a crack propagates through substrate under the conductive paths.

In one aspect, a method of monitoring the structural health of an object having a surface of interest is provided. In one embodiment, the method includes:
 providing a circuit adjacent the surface of the object, the circuit including a plurality of conductive paths disposed adjacent the surface of the object or on a transferable medium bonded to the surface of the substrate;
 obtaining an initial conductive state of the circuit; and
 monitoring an active conductive state of the circuit for deviations from the initial conductive state, wherein a deviation from the initial conductive state is indicative of an interrupted or alteration of conduction of at least one of the plurality of conductive paths.

In another aspect, a system is provided. In one embodiment, the system includes:
 a substrate having a surface; and
 a circuit including a plurality of conductive paths disposed adjacent the surface of the substrate, wherein the circuit is configured to:

detect an interruption or alteration of conduction of one or more of the plurality of conductive paths due to exposure to an environmental change affecting the substrate, and identify the interrupted or altered one or more of the plurality of conductive paths based on one or more electrical characteristics of the circuit.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 11A and 11B depict an embodiment of a circuit disposed directly on a transferable medium that is capable of being bonded to a substrate, in accordance with any of the substrates and circuits described herein.

DETAILED DESCRIPTION

Figure 1A:
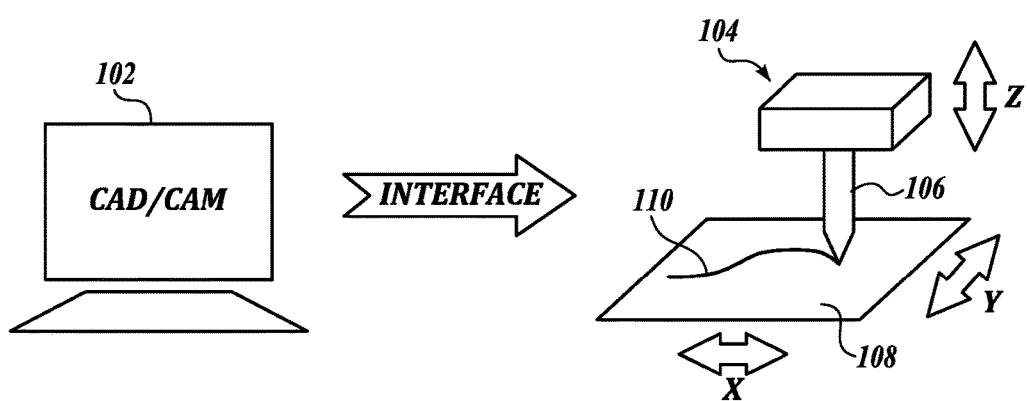
FIG. 1A depicts an example of a direct write (DW) design and write process, in accordance with embodiments disclosed herein.

A novel approach to monitor the health of a structure relies on the use of fuse-like sensors. In this case, sensing networks are placed on "hot spots" (e.g., areas of concern for potential flaws, such as cracks) of a given structure. Once a flaw or crack occurs, the flaw itself will break the sensor or part of it. State-of-the-art fuse-like sensors use micro-channels carved or machined on the host structure surface or on flexible pads. These channels are then encapsulated and vacuum is applied. This technology is called Comparative Vacuum Monitoring (CVM), such as described in (1) Stehmeier, H., and Speckmann, H., "Comparative Vacuum Monitoring (CVM)—Monitoring of fatigue cracking in aircraft structures," Proceedings of the 2nd European Workshop on Structural Health Monitoring, Germany, 2004; (2) Roach, D., Rackow, K., et al., "Use of Composite Materials, Health Monitoring and Self-Healing Concepts to Refurbish our Civil and Military Infrastructure," SANDIA Report, SAND2007-5545, 2007; and (3) LaCivita, K., "Informal Evaluation of Vacuum-Based Crack Detection Sensor," AFRL report, AFRL/MLS 01-076.

Once a crack propagates, it breaks the channel and the vacuum is lost, producing a signal. Some of the problems with CVM are that by fabricating the channels, stress concentrators are created on the part, and crack initiation starts quickly on the host surface. In addition, the vacuum system is complex, and requires a set of hoses and valves that increases weight, and could fail over time (leakage) producing false positive indications.

Direct Write (DW) is an additive manufacturing technique for writing electronic circuits directly on flat or curved surfaces without any special tooling (see Hon, K., Li, L., and Hutchings, I., "Direct writing technology—Advances and developments," CIRP Annals—Manufacturing Technology 57 (2008) 601-620 (hereinafter "Hon")). Material is deposited layer by layer to build up structures or features. This technology is known also as printed electronics. DW is used to print functional electronic circuitry and components directly onto low-temperature and even non-planar substrates such as leading edge wing surfaces. This is in contrast to traditional subtractive manufacturing methods where masking and etching processes are used to remove material to get to the final form. Under this additive manufacturing approach, active and passive elements, placed directly on walls/surfaces, are highly integrated onto the host structure. For example, the thickness of sensing arrays can be between 0.5 μm and 100 μm. DW features can be deposited on flexible films such as polyimide (PI) or Polyether ether ketone (PEEK) and are able to be used as embedded or bonded systems if desired. DW can directly deposit a wide range of commercial and custom electronic materials such as resistors, conductors (copper, silver, gold, etc.), dielectrics, piezoelectrics, carbon nanotubes, adhesives and polymers, among others. With these materials, different sensors, resistors, capacitors, transducers, interconnects, coils, circuiting elements and even antennas can be fabricated or printed.

FIG. 1A depicts an example of a DW design and write process. In FIG. 1A, a computing system 102 includes software, such as computer-aided drafting (or design) (CAD) or computer-aided modeling (or manufacturing) (CAM) software, that aids in the control of the DW process. The computing system 102 accepts user inputs for controlling the DW process and interfaces with a DW system 104. The DW system 104 includes a depositing mechanism 106. The DW system 104 controls movement of the depositing mechanism 106 with respect to a substrate 108, such as translations along one or more of the X, Y, and Z axes and/or rotations about one or more of the X, Y, and Z axes. The DW system 104 also controls selective depositing of material 110 on the substrate 108. In some embodiments, the material 110 includes one or more of resistors, conductors, dielectrics, piezoelectrics, carbon nanotubes, adhesives, polymers, and the like. In some embodiments, the movements of and selective deposition by the depositing mechanism 106 are controlled such that the material 110 on substrate 108 forms electronic circuitry and/or components.

In one aspect, a system is provided. In one embodiment, the system includes:

a substrate having a surface; and a circuit including a plurality of conductive paths disposed adjacent the surface of the substrate, wherein the circuit is configured to:

detect an interruption or alteration of conduction of one or more of the plurality of conductive paths due to a flaw in the substrate, and identify the interrupted or altered one or more of the plurality of conductive paths based on one or more electrical characteristics of the circuit.

Figure 1B:
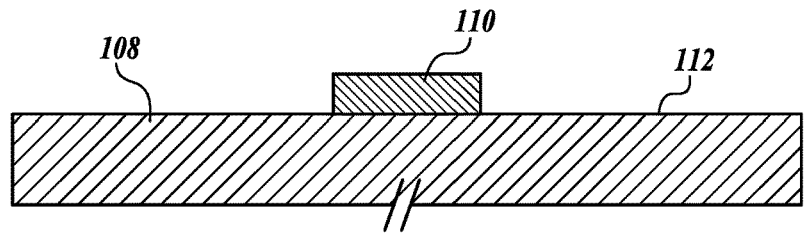
FIGS. 1B and 1C depict cross-sectional views of a substrate with fuse-like material deposited on, respectively, a surface of a substrate and a channel of a substrate, in accordance with embodiments disclosed herein.
Figure 1C:
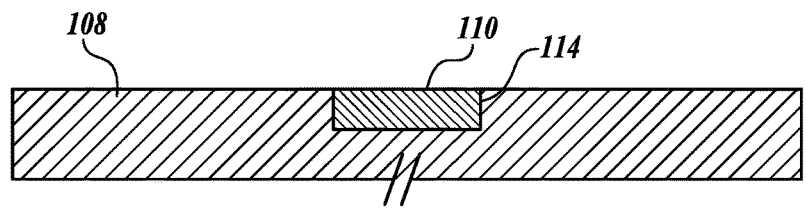

FIGS. 1B and 1C depict cross-sectional views of a substrate with DW material deposited on, respectively, a surface of a substrate and a channel of a substrate. In FIG. 1B, the substrate 108 includes a surface 112. The material 110 is deposited directly on the surface 112 as conductive traces, which provide the "fuse-like" properties of the system. In one embodiment, the thickness of the material (i.e., the height of the material from the surface 112, as shown in FIG. 1B) is controlled based on an amount of the material 110 deposited on the surface 112. In FIG. 1C, the substrate 108 includes a channel 114. The material 110 is deposited in the channel 114. In one embodiment, as shown in FIG. 1C, the material 110 substantially fills the channel 114.

In FIGS. 1B and 1C the substrate 108 is insulating (e.g., plastic), which allows the material 110 to function as a conductor without interference from the substrate 108. Accordingly, in certain embodiments, the substrate 108 is insulating.

Figure 1D:
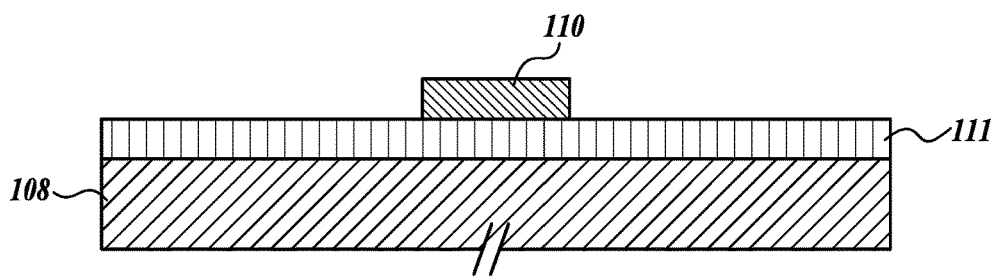
FIGS. 1D and 1E depict cross-sectional views of a substrate with fuse-like material deposited on, respectively, a large-area insulating layer covering a substrate and a patterned insulating layer disposed on a substrate, in accordance with embodiments disclosed herein.
Figure 1E:
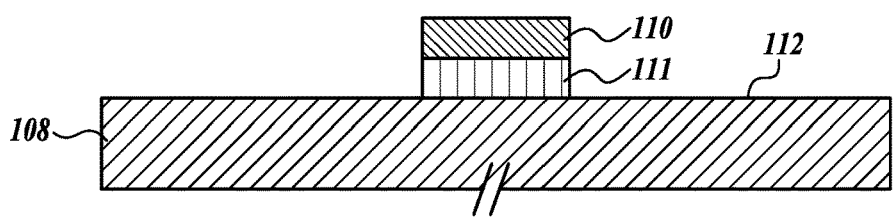

Conversely, in other embodiments, the substrate is conductive (e.g., a metal wing or other surface) or semiconductive. In such embodiments, as illustrated in FIGS. 1D and 1E, the substrate 108 and fuse material 110 are separated by an insulating layer 111. Referring to FIG. 1D, a large-area insulating layer 111 covers the substrate 108 and the material 110 is patterned thereon. In another embodiment, the insulating layer 111 is patterned, either by the same technique as is used to pattern the material 110 or a different technique. In an embodiment, the insulating layer 111 is a material selected from the group consisting of a paint layer, a dielectric layer, a protective layer, and combinations thereof. Exemplary protective layers include an anodized layer of a metal surface and a polymer coating.

Figure 1F:
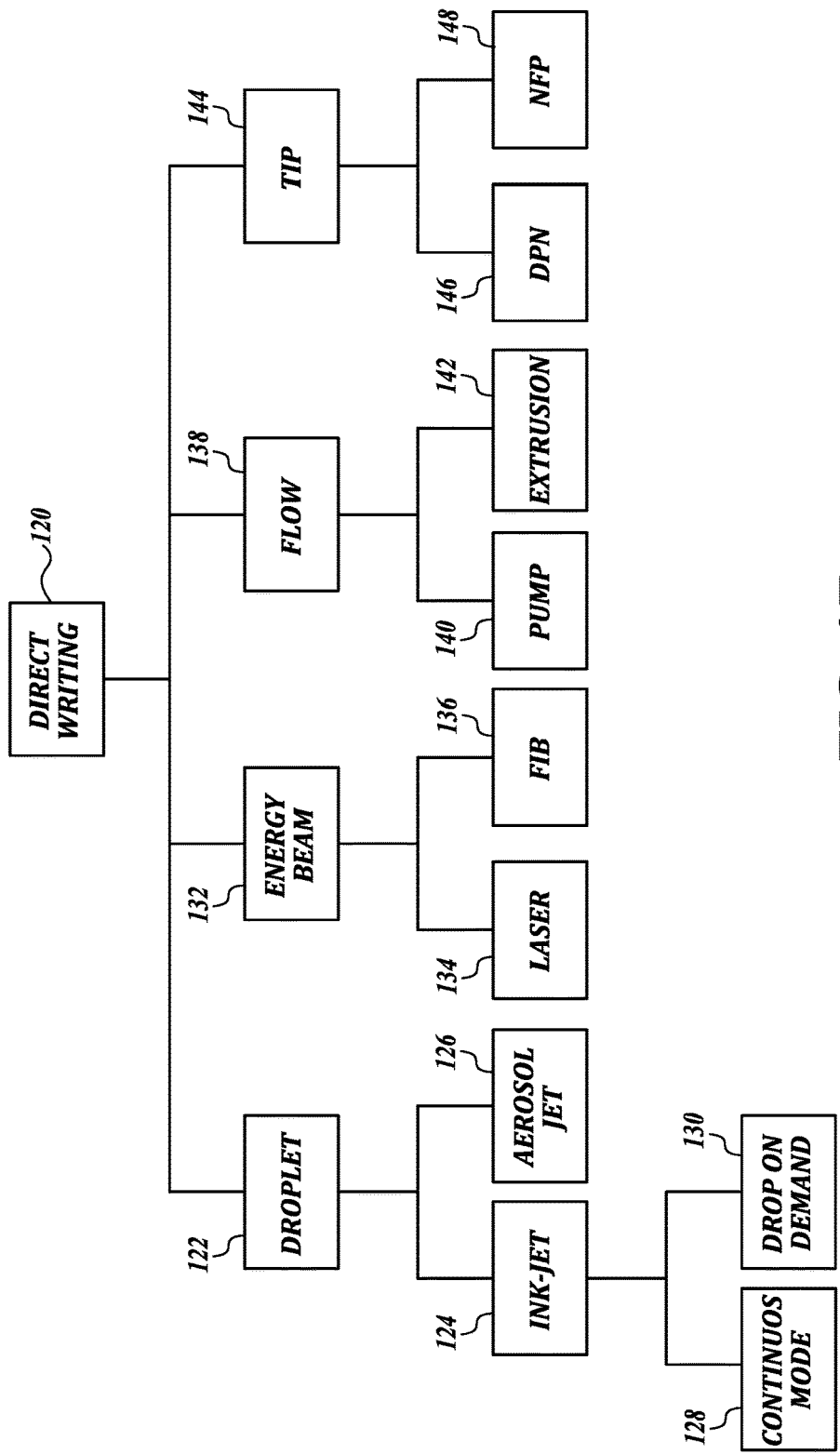
FIG. 1F depicts a diagram with a classification of different DW methods, based on different deposition mechanism, in accordance with embodiments disclosed herein.

DW covers a series of technologies to deposit or transfer a given material onto a substrate. An overview of key DW technologies and their process characteristics is presented in FIG. 1F, which depicts a diagram with a classification of different DW methods 120, based on different deposition mechanisms. In the case of droplet-based methods 122, there are two main approaches: inkjet 124 and aerosol jet 126. Inkjet technology 126 includes both continuous mode 128 and drop-on-demand mode 130. Inkjet technology 126 is the most common form of DW technology and it appeared in the mid-1970s. It is mature, but it requires a close contact with the substrate. On the other hand, aerosol jets 126 are becoming more popular, in part because of the allowed standoff between the nozzle and the tip. This allows non-contact deposition of materials on highly curved surfaces. Regarding energy beam-based techniques 132, a strip of material is transferred, deposited or consolidated by laser beam 134 or an ion beam 136. For flow-based methods 138, high-precision micro-dispensing devices are used to either pump 140 or extrude 142 the material through a small hole or a needle. Finally, tip-based techniques 144 use microcapillary action between the tip and the substrate surface to transfer or diffuse the material. Tip-based techniques 144 include dip-pen nanolithography (DPN) 146 and the use of nanofoundation probes (NFP) 148. In one embodiment, at least a portion of the circuit is printed using a technique selected from the group consisting of aerosol jet direct writing, extrusion printing, ink-jet printing, screen printing, roll printing, gravure printing, and combinations thereof.

It is important to note that screen printing is a very common method to print electronics on flexible and rigid flat substrates. However, screen printing requires the use of a stencil (printing screen) with the etched desired pattern. By definition, the use of the stencil does not comply with the DW definition. Methods that use engraved surfaces, dies, or pads also do not constitute DW even though they are additive manufacturing methods. The concepts presented herein can be applied to any DW and/or additive manufacturing method that can conform to single or double curvature surfaces.

One particular DW method is Aerosol Jet (AJ) printing. Here, an aerosol of fine ink droplets is created by pneumatic or ultrasonic methods and propelled in a gas stream toward the substrate. The AJ process utilizes an innovative aerodynamic focusing technique known as a sheath gas to collimate this dense aerosol mist of material-laden micro-droplets into a tightly controlled beam of material that can produce features as small as 5 μm (or as large as several centimeters). Coupled with a motion control system that moves either the head or the substrate, high resolution patterns (e.g., +/−1 μm) can be created using CAD drawings to produce electronic, physical and optical structures, as well as wide area conformal coatings. Because ink flow is held constant, undesirable material is collected by a programmed shutter arm. With varying sizes of print-head nozzles 100, feature sizes as small as 10 μm (<10 μm with optimization) are capable even with high viscosity (up to 2500 cP), high solids content (≥60 wt %) inks, which is well beyond the range of conventional inkjet writing. The process is non-contact, enabling traces to be printed over steps, curved surfaces, and conformally on non-planar objects while printing with a standoff distance of up to 5 mm. Line widths of printed features are controlled by various parameters such as gas flow ratios, temperature, and substrate velocity. In principle, virtually any substrate can be used, provided it is compatible with the ink. The AJ printing system can be equipped with NIR laser for sintering nanoparticle inks on substrates sensitive to high temperatures (>120° C.). For laser curing processes, the jetted features are subjected to the same toolpath as for deposition yet under a controlled focused laser beam. The laser can be adjusted by controlling power output (50-1000 mW) and velocity. By using multiple printing heads, the AJ throughput can be increased considerably and can be integrated with roll-to-roll printing technologies for mass production. The fundamental system building blocks have shown the potential to be highly flexible in terms of their ability to support low/high viscosity inks, produce thin/thick layers, print small/large features, etc. Aerosol Jet printing is a breakthrough technology that is an emerging replacement for traditional thick-film processes like screen-printing, photolithography and micro-dispensing, as well being far more robust than emerging inkjet printing solutions.

After the printing process, the deposited structures must be thermally treated to activate the functionality. Of course, the solvent has to evaporate before curing or sintering the ink. Subsequently, the thermal treatment can be done by conventional furnace sintering if the substrate can tolerate the sintering conditions. Localized heating methods, such as microwave, photonic curing, and laser sintering are promising approaches with only a minor impact on the substrate. It should be noted that a limiting factor is the Glass Transition Temperature (Tg) or Melting Temperature (Tm) of the substrate (metals, plastics, composites, or ceramics).

Fuse-Like Sensor Concepts

Due to the lightweight detailing and sometimes intricate contours and shapes of the host structure, hot spots are difficult to inspect/interrogate during usage and monitor over the lifetime of the part. Most interrogation equipment adds significant weight or is difficult to adhere to the host structure. A novel approach to monitor the health of a structure relies on the use of fuse-like sensors. In this case, sensing networks are placed on "hot spots" (e.g., locations of potential flaws) of a given host structure. In certain embodiments, the sensing networks are placed permanently on such a hot spot. Once a flaw or a change of state occurs, the flaw itself will break or modify irreversibly the physical and/or chemical properties of the sensor or sensing network. In addition, by using a given array of fuse-like sensors such as a linear or radial array with known dimensions, flaw sizing can be determined. As result, a fuse-like system is capable not only of indicating the presence of a flaw of change of state, but also providing an indication of its size, magnitude and event orientation and shape. Power and electronics for interrogation and processing can be installed on the host structure or externally. With fuse-like sensors, one drawback of not having the electronics installed and/or connected at all times is that it can only be used for periodic monitoring. However, the system is light and certification for installation and operation is simpler than certification for full structural health monitoring systems. In certain embodiments, however, permanent monitoring with fuse-like sensors is possible if a permanent wiring scheme is possible, or if wireless transmission of monitoring data is used.

In embodiments disclosed herein, a direct write fuse-like sensor that does not affect mechanically or chemically the surface of the host structure is described for structural integrity assessment. The main advantage of this approach is that the fuse lines are very close (0.1 µm to 2 µm) to the host surface allowing for the fuses to follow the mechanical behavior of the substrate properly. As a result, the fuse-like sensor is more sensitive, accurate, and reliable than state-of-the-art solutions. In addition, printed fuse-like sensors can be placed inside multi-layer assemblies due to their low thickness (1 µm to 150 µm).

Embodiments of fuse-like sensors described herein have a set of fuses that are concentric rings, parallel lines, or have any kind of array configuration, pattern and shape that surround or abut an area of interest. The fuses can be also positioned on a given path or region where the flaw or abnormality can occur. The fuses are made of electrically conductive traces and are connected to a connection point where they will be connected to an electronic unit for monitoring or interrogation. Between the connector and the fuses, a resistor can be placed. Each fuse has an associated resistor that is different in resistance value. The resistors can be created by using the same material as the trace, or a material with different electrical resistivity properties. Resistors can be placed in series or in parallel depending on the fuse-like sensor configuration. In another fuse-like configuration, each trace is made of a material that has different electromagnetic properties such as resistance, capacitance, and/or inductance. In another configuration, the fuses can have different line width and thickness to produce different electromagnetic properties, such as resistance, capacitance, and/or inductance. In another configuration, the traces can have the resistors printed on one part or along the traces. In another sensor configuration, the resistors can be removed from the fuse-like sensor and placed on the reading instrument. In this case, the number of connections for the sensors is equal to the number of traces plus one line for ground.

Figure 2A:
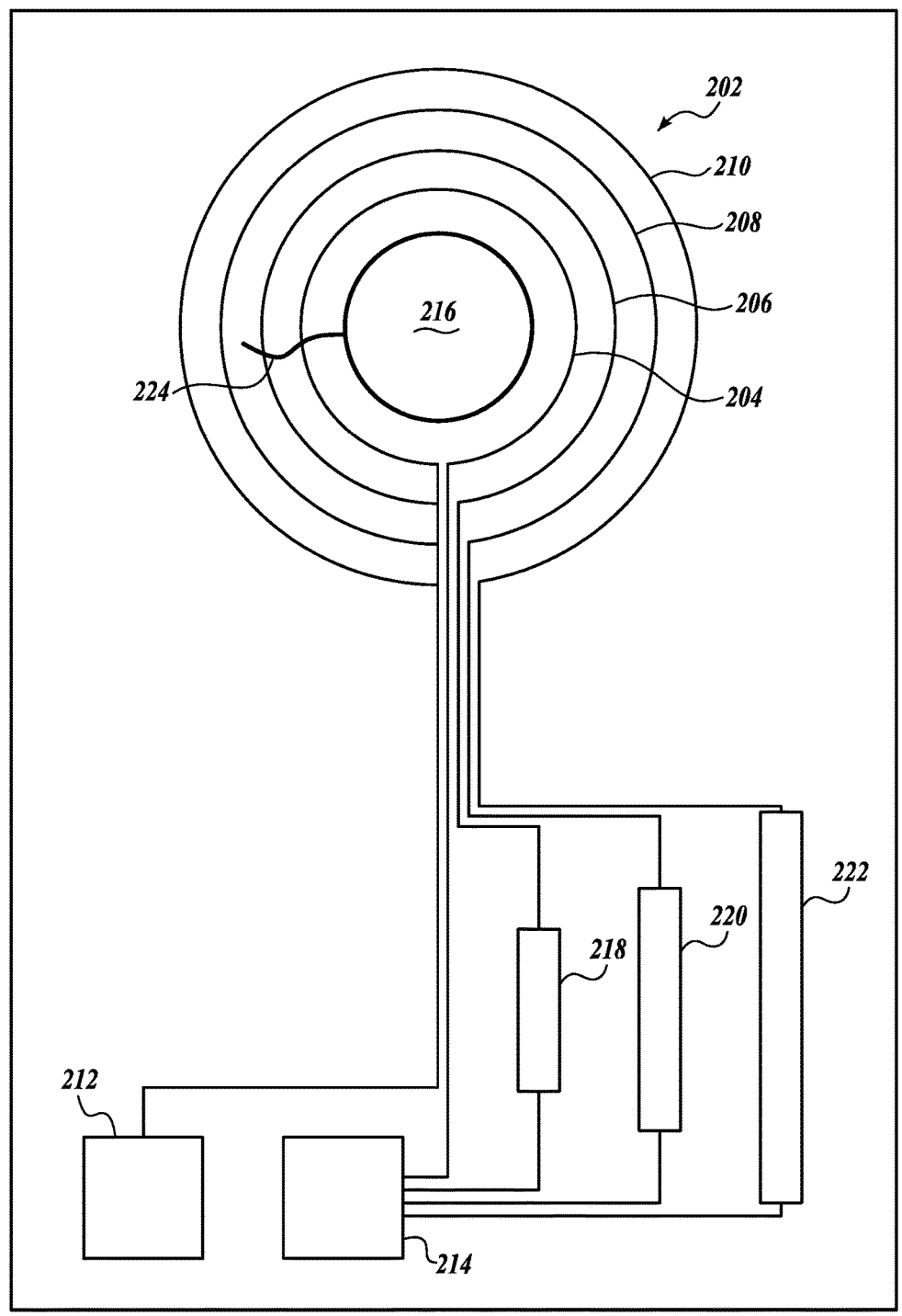
FIGS. 2A and 2B depict examples of sensor patterns printed on test samples, in accordance with embodiments disclosed herein.
Figure 2B:
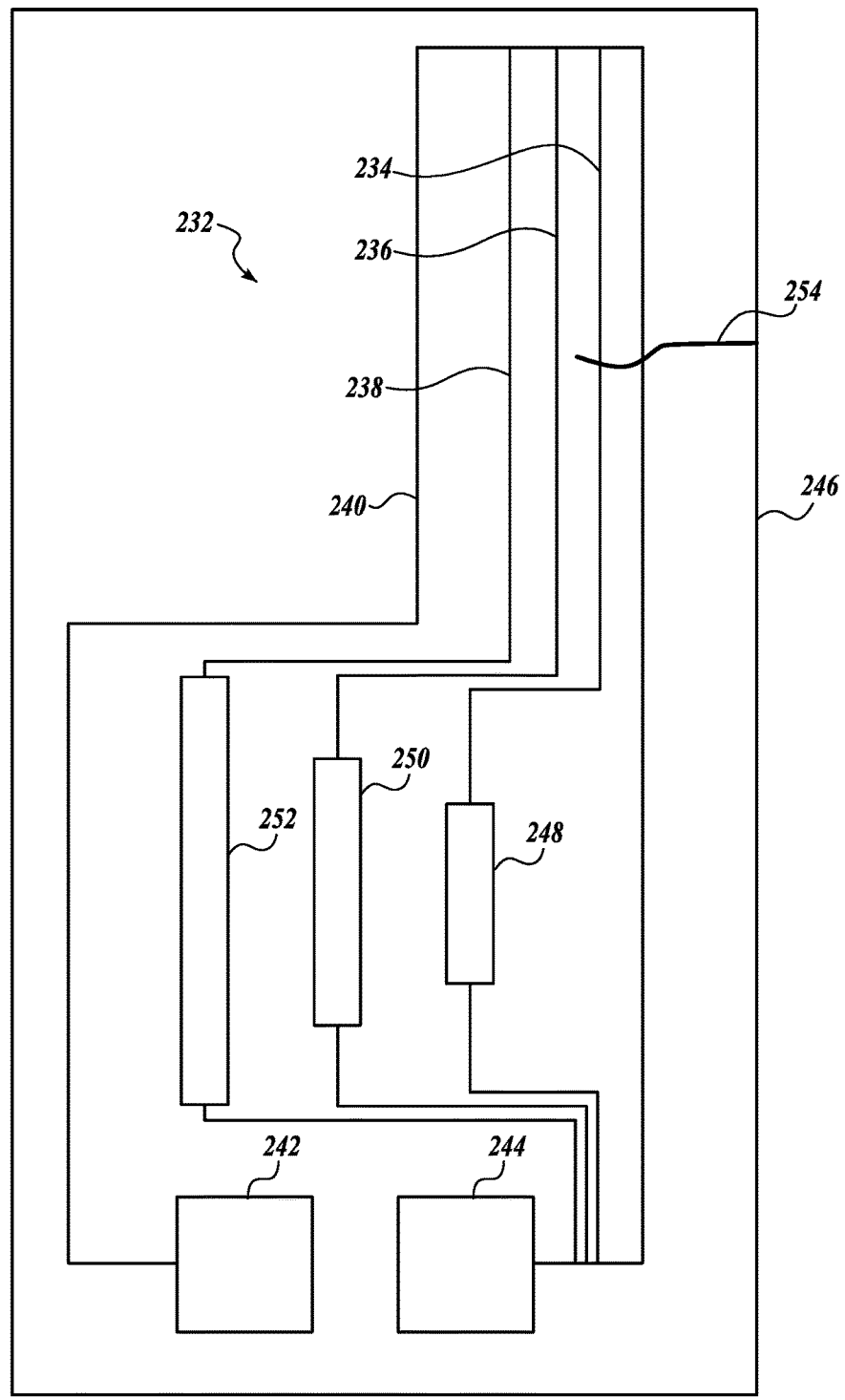

Examples of sensor patterns printed on test samples are depicted in FIGS. 2A and 2B. In FIG. 2A, a sensor pattern 202 that has been deposited on a sample by a DW process. The sensor pattern 202 includes four parallel paths 204, 206, 208, and 210 between two electrodes 212 and 214. In some embodiments, the parallel paths comprise conductive materials, semi-conductive materials, or some combination thereof. Electrical conductivity of semi-conductive materials is typically in a range from about $10^3$ to about $10^{-9} \Omega^{-1} \cdot cm^{-1}$. Electrical conductivity of conductive materials are typically greater than electrical conductivity of semi-conductive materials and electrical conductivity of insulative materials are typically less than electrical conductivity of semi-conductive materials. Portions of the four parallel paths 204, 206, 208, and 210 are arranged as concentric circles around a hole 216 in the sample. The sensor pattern 202 also includes printed resistors 218, 220, and 222 that are located, respectively, on the parallel paths 206, 208, and 210. The printed resistors 218, 220, and 222 have different values such that the resistances R1, R2, R3, and R4 in the respective four parallel paths 204, 206, 208, and 210 are different. In one embodiment, the resistance of the printed resistors 218, 220, and 222 are selected such that R1<R2<R3<R4.

Electrical measurements can be taken between the two electrodes 212 and 214. Current will flow in the sensor pattern 202 between the two electrodes 212 and 214 along the path of least resistance. In the case where R1<R2<R3<R4, the current will flow along path 204 because it has the least resistance. However, a crack 224 or other flaw (e.g., strain, plastic deformation, elastic deformation, etc.) may develop in the sample and propagate from hole 216. If the crack 224 interrupts or alters conduction in the path 204, then the least resistant path becomes path 206;

if the crack 224 interrupts or alters conduction in the paths 204 and 206 (as shown in FIG. 2A), the least resistant path becomes path 208; and so forth. In this way, with known values of the printed resistors 218, 220, and 222, electrical measurements taken between the two electrodes 212 and 214 can be used to determine whether a crack 224 is propagating from the hole 216 and how far the crack 224 has propagated from the hole 216. The measurements can be taken by a single source of voltage and/or current.

In FIG. 2B, a sensor pattern 232 that has been deposited on a sample by a DW process. The sensor pattern 232 includes four parallel paths 234, 236, 238, and 240 between two ends 242 and 244. Portions of the four parallel paths 234, 236, 238, and 240 are arranged physically parallel to an edge 246 of the sample. The sensor pattern 232 also includes printed resistors 248, 250, and 252 that are located, respectively, on the parallel paths 234, 236, and 238. The printed resistors 248, 250, and 252 have different values such that the resistances R1, R2, R3, and R4 in the respective four parallel paths 234, 236, 238, and 240 are different. In one embodiment, the resistances of the printed resistors 238, 240, and 242 are selected such that R1<R2<R3<R4.

Electrical measurements can be taken between the two ends 242 and 244. Current will flow in the sensor pattern 232 between the two ends 242 and 244 along the path of least resistance. In the case where R1<R2<R3<R4, the current will flow along path 234 because it has the least resistance. However, a crack 254 may develop in the sample and propagate from the edge 246. If the crack 254 interrupts or alters conduction in the path 234, then the least resistant path becomes path 236; if the crack 254 interrupts or alters conduction in the paths 234 and 236 (as shown in FIG. 2B), the least resistant path becomes path 238; and so forth. In this way, with known values of the printed resistors 248, 250, and 252, electrical measurements taken between the two ends 242 and 244 can be used to determine whether a crack 254 is propagating from the edge 246 and how far the crack 254 has propagated from the edge 246.

Figure 2C:
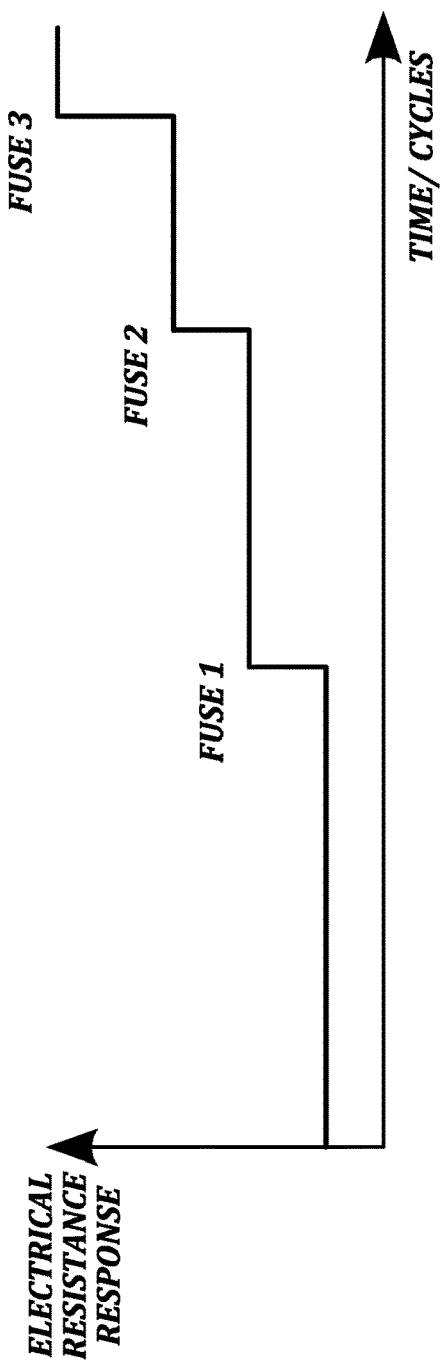
FIG. 2C depicts an example electrical resistance response versus time or fatigue cycle, in accordance with embodiments disclosed herein.

In one embodiment, when a crack or flaw breaks one of the fuses of a fuse-like sensor, the electromagnetic response of the sensor varies. In the case of cracks, the best sensor configuration uses thin printed lines or fuses close to the host substrate. When a crack on the host encounters a fuse or trace, it will break the fuse or trace and interrupt the passage of electrical current through that fuse or trace. FIG. 2C depicts an example electrical resistance response versus time or fatigue cycle.

In another embodiment, an additional resistor can be placed between the main contact points near the sensing fuses. This resistor is used to detect if a flaw has propagated through the external fuse element. By reading the electrical resistance of the fuse-like sensor circuit, it is possible to define whether a detected flaw is real or if there is damage on the sensor. The use of DW allows a reduction in weight, costs, manufacturing steps, loose parts, and vibration while offering quality benefits and high flexibility for designing and fabricating fuse-like sensing systems. In addition, the system can be placed on any type of material and/or structure topology. The performance of the fuse-like sensor can be characterized in terms of structural and electrical properties, for example sheet electrical resistance, accuracy, reliability, and durability among others. Based on the nature of the host structure material, the ink or material chemistry used to direct write or deposit the sensors can be optimized for printing, functionality, and durability. The benefit of using functional inks (particle diameter<500 nm) is the high ratio of surface to volume. This means that nanoparticles ranging from 1 to 100 nm have a much lower effective melting point and sintering temperature compared to their bulk material. Therefore, fine structures with dimensions of only a few microns can be precisely printed allowing for a wide range of geometrical patterns, offsets and topologies. Finer patterns provide better resolution to size cracks and flaws. These capabilities are very powerful to print fuse-like sensors where the system can have a crack length resolution about 5 µm to 10 µm. The formulation of a suitable ink is a critical phase, as the performance or quality of the printing process strongly depends on the ink. Apart from DW, it can be noted that the fuse-like sensors can be produced using traditional thick-film processes like screen-printing, photolithography and micro-dispensing, as well as other emerging inkjet printing solutions and DW processes, such as e-beam. Thanks to the non-contact nature of some DW processes, such as AJ, the fuse-like sensors can be placed not only on planar substrates but on highly curved surfaces. These curved surfaces can be convex or concave and have single curvature or double curvature.

Figure 3A:
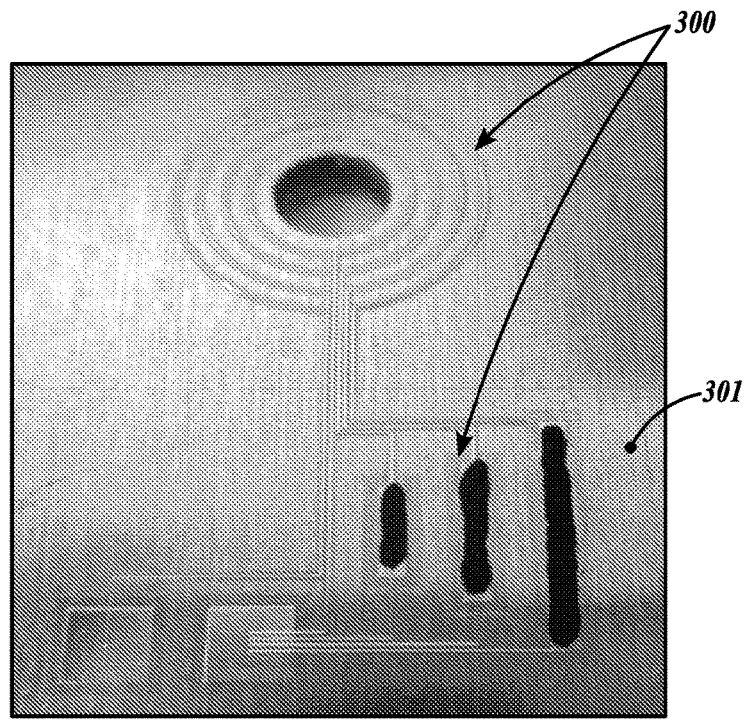
FIGS. 3A and 3B depict, respectively, a full view and a detail view of an exemplary sample that has a deposited sensor pattern similar to the sensor pattern depicted in FIG. 2A, in accordance with embodiments disclosed herein.
Figure 3B:
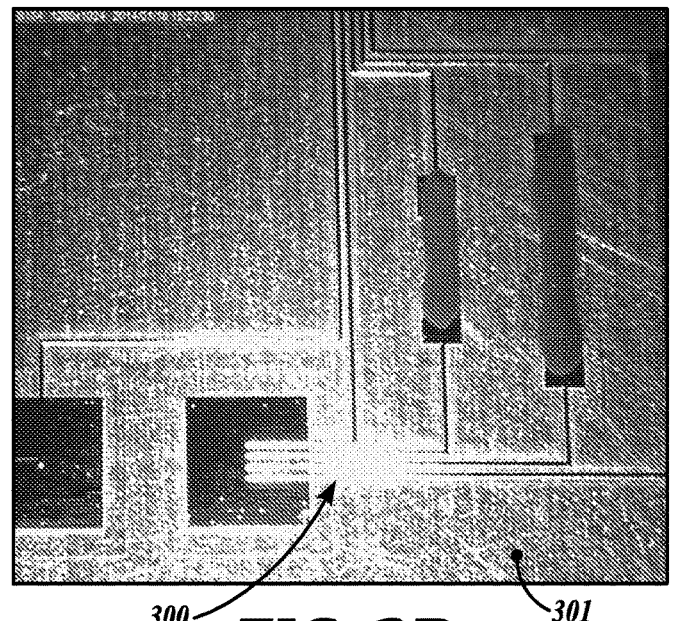
Figure 4A:
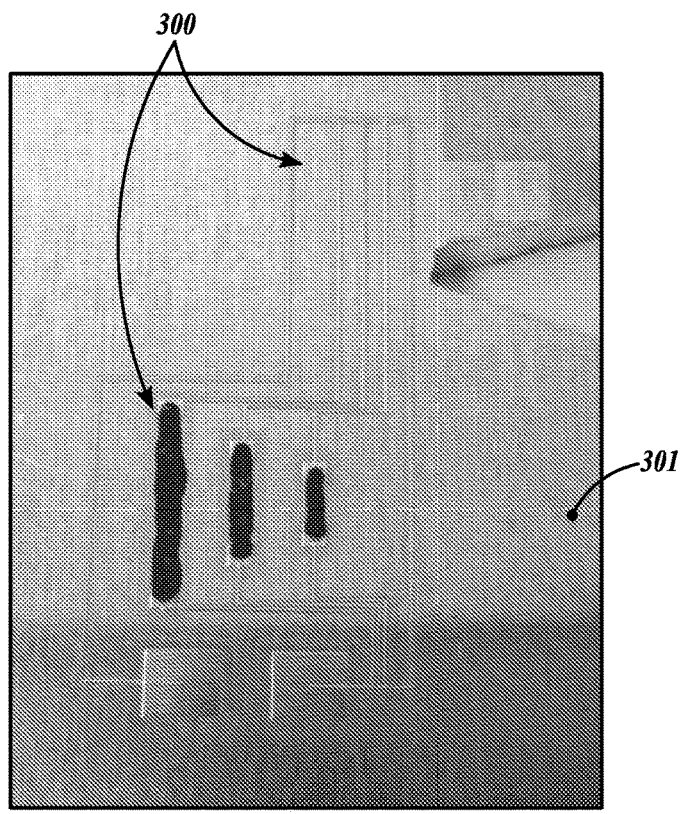
FIGS. 4A and 4B depict, respectively, a full view and a detail view of an exemplary sample that has a deposited sensor pattern similar to the sensor pattern depicted in FIG. 2B, in accordance with embodiments disclosed herein.
Figure 4B:
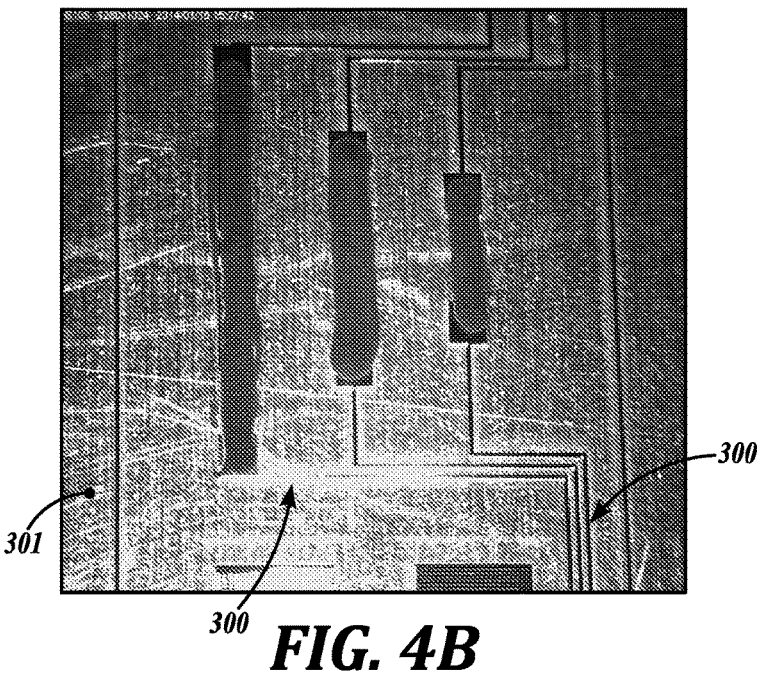

Exemplary printed fuse-like sensors using DW are depicted in FIGS. 3A, 3B, 4A, and 4B. FIGS. 3A and 3B show, respectively, a full view and a detail view of a sample that has a deposited sensor pattern similar to the sensor pattern 202 depicted in FIG. 2A. FIGS. 4A and 4B show, respectively, a full view and a detail view of a sample that has a deposited sensor pattern similar to the sensor pattern 232 depicted in FIG. 2B.

In the designs shown in FIGS. 3A, 3B, 4A, and 4B, AJ was used as means of printing conformal, functional, unobtrusive structural fuse-like health monitoring systems 300 on metallic structures 301. Sensors or sensing patterns were drafted in a CAD program to conform to different regions where cracks may form. Both patterns involve multiple fuses in parallel to identify crack formation and/or crack propagation. In these designs, the formation of a critical crack size will break the first fuse, any further propagation of the crack is monitored by the sequential fuse layers set at specified distances. The identification and measurement of the crack size is based on electrical resistance of each fuse. The sensor is designed in a manner that the electrical measurement will follow the path of least resistance. Therefore, each ring or layer of the fuse is fabricated with a printed resistor of a known value. With each increasing fuse layer, the resistance of the sensor increases so that R1<R2<R3<R4. Unlike other assembly methods, this additive manufacturing process includes three non-invasive steps: (1) cleaning and preparation of the sample, (2) material deposition, and (3) curing the printed features. In some applications, the fuse-like sensors can be deposited on a transfer substrate for easy installation on complex or difficult to access areas. Printed fuses were fabricated with a polyimide thermoset resin, acting as a dielectric (insulating) material, a low temperature curing silver (Ag) nanoparticle ink (sheet resistance 0.010Ω/☐), and a carbon paste to act as a resistive material (sheet resistance 50Ω/☐). The polyimide resin was first deposited on aluminum coupons to insulate the printed fuses from the conductive metallic structure. Once printed, the polymer was thermally cured at 150° C. Polyimide exhibits exceptional adhesion to nearly all metal surfaces and provides a bondable surface with low coefficient of thermal expansion for the printed fuses.

It is understood that the adhesion of printed parts to the sample is essential for the crack causing deformation to signal a positive reading from the fuse. Therefore, the newly formed polyimide surface was plasma treated to promote adhesion of the printed conductive fuses. Plasma treatments significantly increase the surface energy of a material by producing an atomically uniform surface, free from any organic contaminants.

Next, the silver nanoparticle ink was printed onto the polyimide feature to produce fuses with a trace width of 0.004" and pitch of 0.040". Once deposited, the silver nanoparticles needed to be sintered to form a conductive system; the sintering process causes the silver nanoparticles to melt together to form near bulk material properties. Sintering included a 30 minute dwell time in a vacuum oven at 150° C. The silver ink includes polymer binding agents such as polyvinylpyrrolidone (PVP) and polyvinyl butyral (PVB), commonly used in inks and paints as it bonds to nearly any surface. These binding agents do not degrade at sintering temperatures, but 150° C. is sufficient to drive off all solvents and capping agents on the silver nanoparticles.

The resistors in parallel were designed in a way that, as the fuse distance increases, so does the resistor value. To contrast the resistance values best, the printed resistors double sequentially in length. R1 was made solely as a silver trace. R2, R3, and R4 were fabricated with a carbon paste with each resistor value changing by the length of the printed resistor; R2 was 0.080", R3 was 0.160", and R4 was 0.320" in length. Once deposited, the carbon paste was cured at 150° C.

Figure 5A:
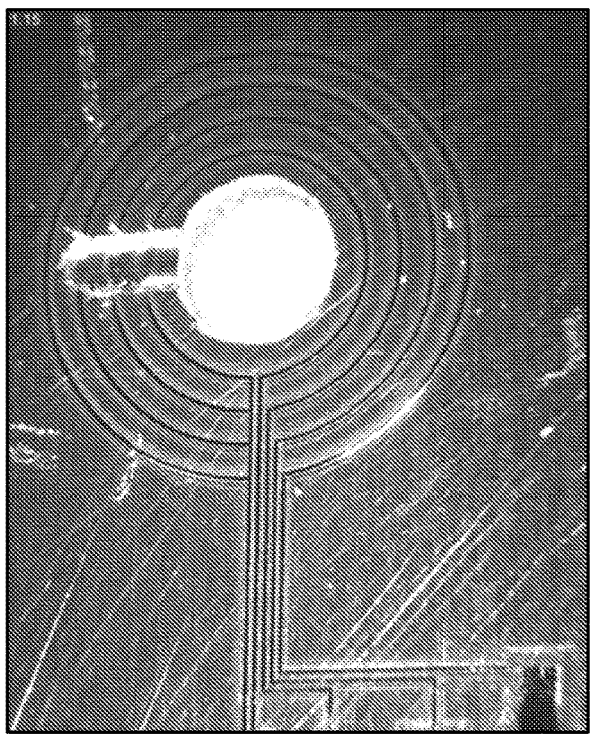
FIGS. 5A and 5B depict simulated crack propagation from, respectively, the rivet hole shown in FIGS. 3A and 3B and the notch shown in FIGS. 4A and 4B, in accordance with embodiments disclosed herein.
Figure 5B:
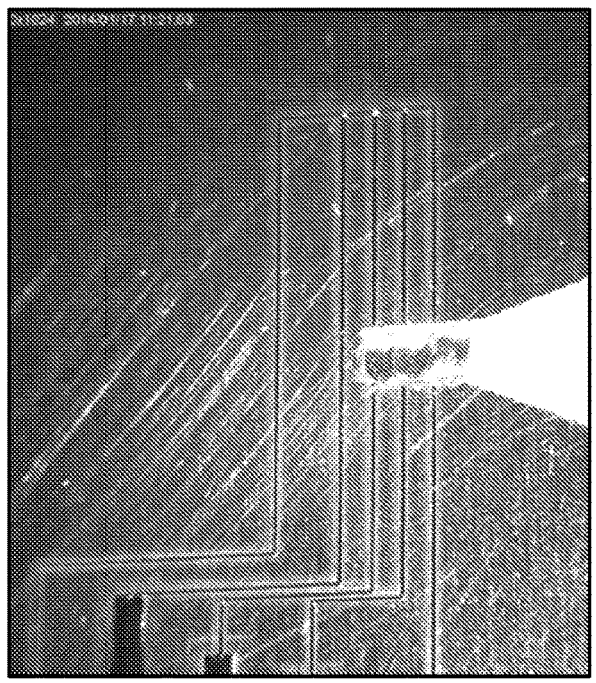

The finished sensor shown in FIGS. 3A and 3B includes a ³⁄₁₆" hole centered in the rings to simulate a rivet or hole-like structure. The distance between the edge of the hole and first fuse layer is 0.040". The detail view in FIG. 3B further illustrates the polyimide, silver, and carbon layers printed on the aluminum sample. FIGS. 4A and 4B depict a sensor design up against a notch in the sample. The distance between the notch and first fuse in FIGS. 4A and 4B was also 0.040". The samples were then staged to simulate a near surface crack propagating through the fuse layers to demonstrate the change in electrical performance across the sensor. FIGS. 5A and 5B depict simulated crack propagation from, respectively, the rivet hole shown in FIGS. 3A and 3B and the notch shown in FIGS. 4A and 4B. A drill press (¹⁄₁₆" drill bit) with micropositioners was used to damage the discrete fuse layers selectively. Crack simulation only removed 0.010" of material, though thinner would have been sufficient. To identify the crack length, resistance values were taken at each 0.04" increment. The resistance values are listed in Table 1. In the particular instances shown FIGS. 5A and 5B, both the simulated cracks are at 0.160-0.199" in length. It is clear that, depending on the materials used to fabricate the traces and resistors, the resistances values can vary between 0.01Ω and the MΩ range.

In some embodiments, for prolonged durability of the printed sensor in harsh environments, a thermoset resin or other suitable encapsulant material would be printed over the conductive and resistive materials.

Figure 6:
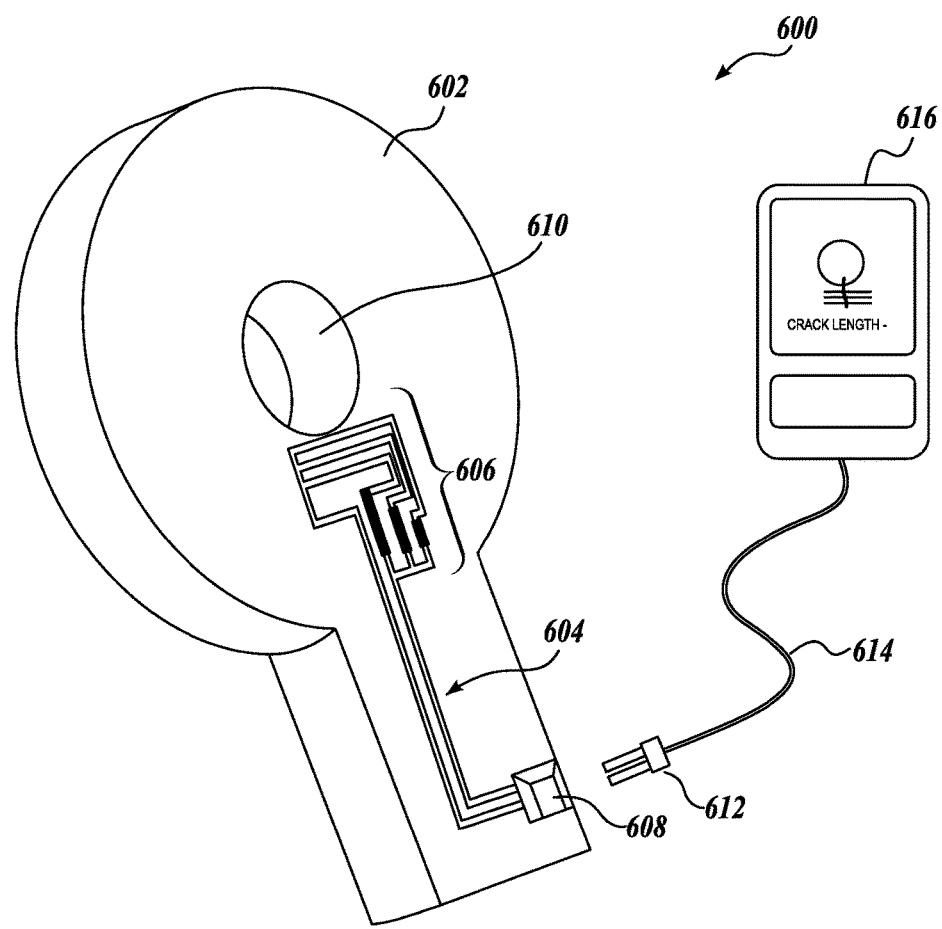
FIG. 6 depicts an embodiment of a fuse-like sensing system with a connector printed or wired at the end of a printed sensor array, in accordance with embodiments disclosed herein.

To interrogate the fuse-like sensing system, in one embodiment of a health monitoring system 600 shown in FIG. 6, a connector is printed or wired at the end of a printed sensor array. More specifically, FIG. 6 depicts a sample 602 with a circuit 604. The circuit 604 includes parallel paths 606, each of which has a different resistance value, and a connector 608. Portions of the parallel paths 606 are located near a hole 610 in the sample 602 in order to detect flaws (e.g., a crack or strain) propagating from the hole 610. In various embodiments, the connector 608 is either a printed connector or a non-printed connector that is wired to portions of the circuit 604. In other embodiments, other components are also printed as part of the circuit, such as a binary weighted ladder digital-to-analog (D-A) conversion circuit. In another embodiment, after the circuit 604 is printed onto the surface of the sample 602, all or a portion of the circuit 604 is covered by an encapsulating material. Some or all of the circuit 604 is located between the surface of the sample 602 and the encapsulating material such that the encapsulating material protects the circuit 604 from physical damage. In one example, the encapsulating material is a polymeric film.

In the embodiment shown in FIG. 6, the connector 608 is configured to be electrically and mechanically coupled to a mating connector 612. The mating connector 612 is in communication, via cable 614, to an external ground interrogation system 616 (e.g., a handheld computing device, a tablet computing device, a laptop computing device, a desktop computing device, etc.). This connector 608, mating connector 612, and cable 614 allow the interrogation system 616 to communicate with the circuit 604 to determine whether a flaw is propagating from the hole 610 and/or to monitor propagation length of a flaw from the hole 610. A measured feature of the circuit 604 (e.g., electrical, resistive, capacitance, etc.) indicates the presence or absence of a flaw (e.g., a crack) and the estimated dimension based on the sensor topology. In other embodiments, the circuit 604 is communicatively coupled, via connector 608, to an on-board interrogation system. In other embodiments, the circuit 604 is configured to wirelessly communicate with an interrogation unit.

Figure 1G:
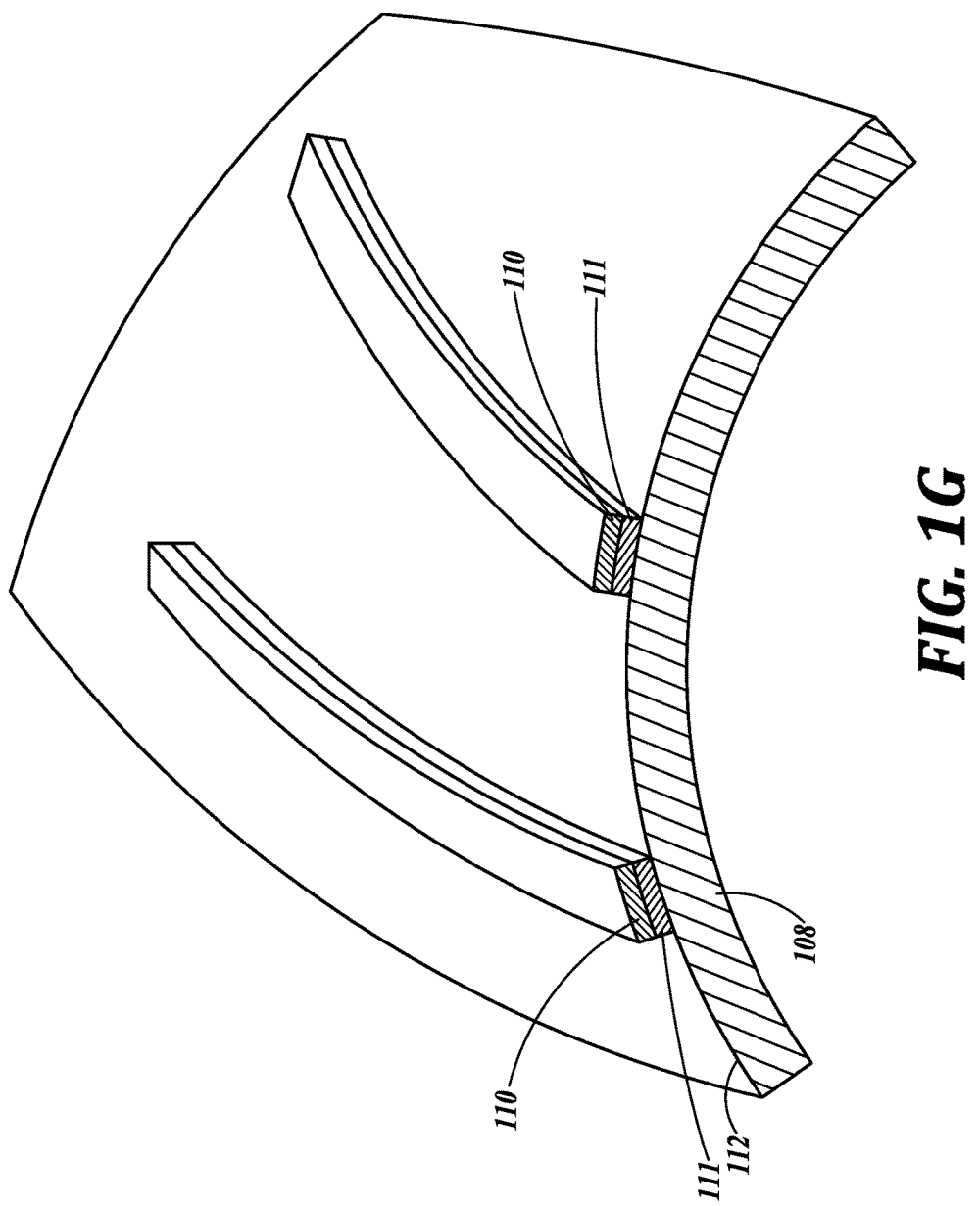
FIG. 1G depicts an isometric view of fuse-like material deposited over a three-dimensional contour of a substrate in accordance with embodiments disclosed herein.

In the embodiment shown in FIG. 6, the surface of the sample 602 with the circuit 604 is relatively flat. In other embodiments, a circuit may be printed on a curved surface (i.e., a surface with a three dimensional contour) as shown, for example, in FIG. 1G. In this case, the circuit printed on the curved surface also follows the three-dimensional contour of the surface.

In one example, fuse-like sensors are capable of being used to monitor surface cracks on any type of material and/or structure topology. In one example, the sensor is part of a structural health monitoring system that monitors an object that includes the substrate. In one embodiment, object is an aircraft component, a building component, a bridge component, or a pipeline component 602. In another embodiment, the structural health monitoring system determines a life expectancy of the object based on data from the circuit.

In another example, the sensors can be printed around fasteners on the external surface. In another example, the fuse-like sensors can be placed on the internal surface. In

TABLE 1

Resistance of exemplary system after simulated cracking of each fuse layer

| Fuse (resistor) | R-Baseline | R1 | R2 | R3 | R4 |
|---|---|---|---|---|---|
| Crack Length | 0.000-0.079" | 0.080-0.119" | 0.120-0.159" | 0.160-0.199" | >0.200" |
| Rivet 1 | 59 Ω | 138 Ω | 237 Ω | 721 Ω | ∞ Ω |
| Notch 1 | 28 Ω | 105 Ω | 271 Ω | 744 Ω | ∞ Ω | another example, the fuse-like sensors can be placed inside of a multi-layer structure assembly. In another example, the fuse-like sensors can be deposited on flat or curved surfaces such as blades, shafts, landing gears, ribs, beams, and gears among others. In another example, the fuse-like sensors can be placed on composite structures to identify disbond, cracks, delamination, or any other flaws.

In another example, by selecting the appropriate fuse material conductive lines, material resistors, and/or material encapsulants, fuse-like printed sensors can monitor flaws on structures at any temperature. For example, by using PI inks, it is possible to reach working temperatures on the order of 350° C. By using ceramic materials and oxides, working temperatures can be on the order of 1000° C. or more.

In another example, the fuse-like sensors can be deposited on a soluble substrate and be used to transfer the sensing pattern onto a host structure. The sensors can be printed on thin adhesive films and applied onto host structures, like a tattoo.

In another aspect, a system is provided. In one embodiment, the system includes:

a substrate having a surface; and a circuit including a plurality of conductive paths disposed adjacent the surface of the substrate, wherein the circuit is configured to:

detect an interruption or alteration of conduction of one or more of the plurality of conductive paths due to exposure to an environmental change affecting the substrate, and identify the interrupted or altered one or more of the plurality of conductive paths based on one or more electrical characteristics of the circuit.

In such embodiments, conductive traces on the fuse-like sensors are configured to detect an interruption or alteration of conduction of one or more of the plurality of conductive paths due to exposure to an environmental change affecting the substrate. In one embodiment, the exposure to environmental change affecting the substrate is at least one of humidity, water, fuel, hydraulic fluids, corrosive conditions, or any other type of desired chemical compound. In that case, the fuse material is selected to react under the presence of the target compound or condition and then breaks or changes resistance significantly. As a result, the electromagnetic response of the printed fuse-like sensor changes to produce an identifiable signal, such as a change in resistance, capacitance, magnetic response, impedance, and/or optical response.

Other Fuse-Like Sensor Concepts

Figure 7A:
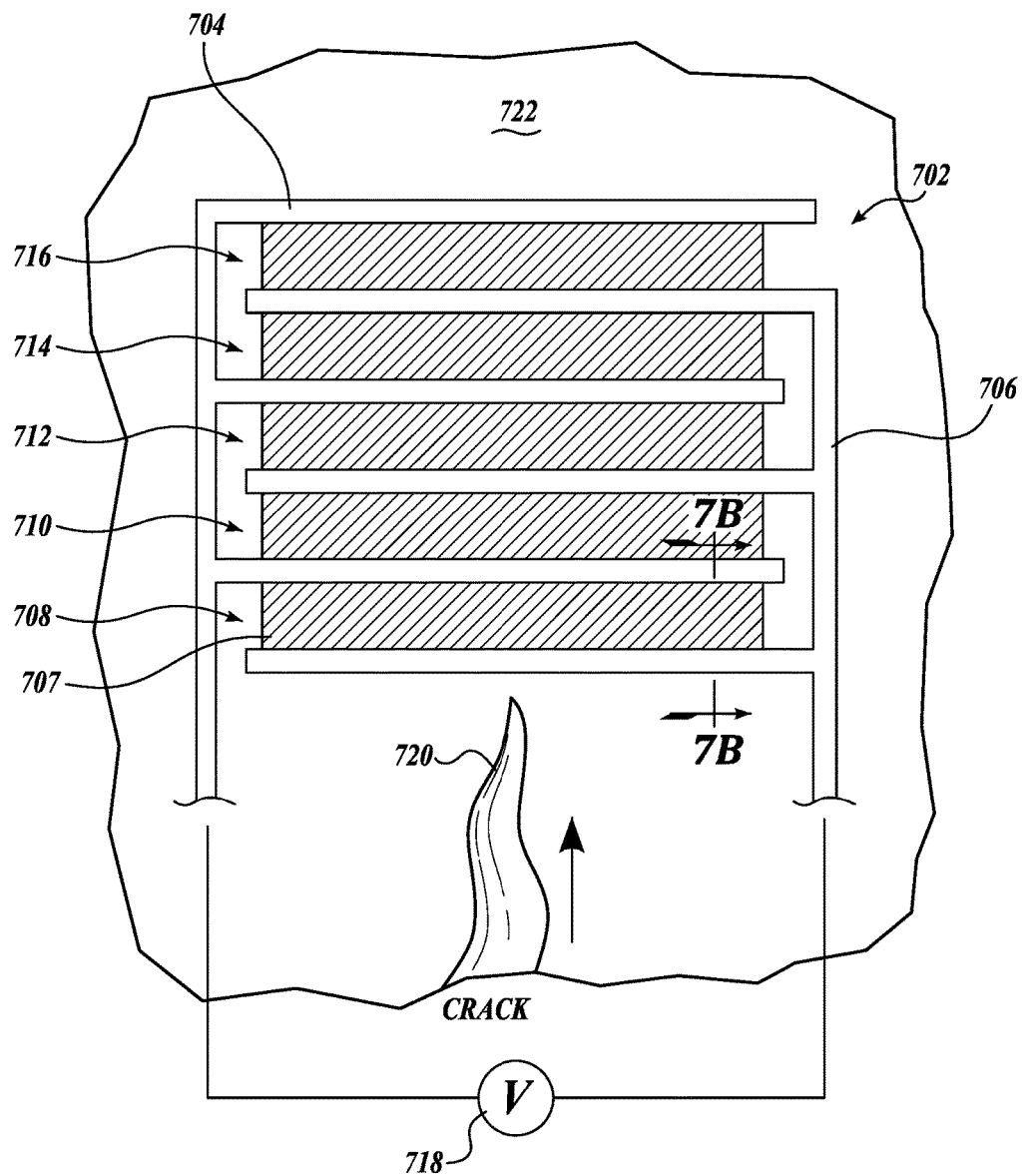
FIGS. 7A and 7B depict top and cross-sectional views, respectively, of an embodiment of a capacitance-based fuse-like sensor, in accordance with embodiments disclosed herein.
Figure 7B:
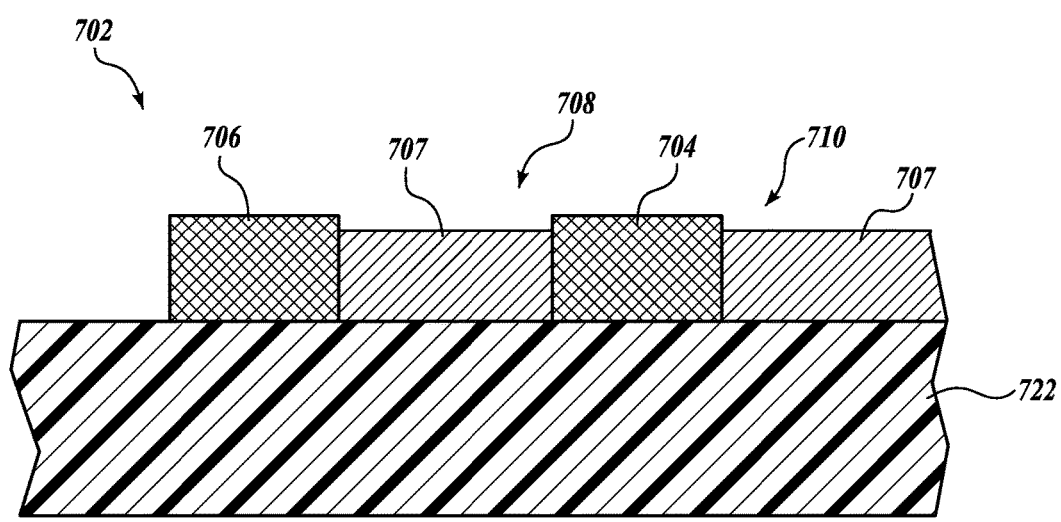

A fuse-like sensing concept can also be based on capacitance, as is disclosed in additional aspects herein. In this regard, FIGS. 7A and 7B depict top and side-elevation cross-sectional views, respectively, of an embodiment of a capacitance-based fuse-like sensor 702. As shown in FIG. 7A, the sensor 702 contains two conductive electrodes 704 and 706 that have interdigitated conductive fingers. The fingers of conductive electrodes (conductive traces) 704 and 706 are separated by dielectric material 707 in separate regions 708, 710, 712, 714, and 716 to form a number of capacitor layers arranged in parallel. As the capacitor layers lie in parallel, the total capacitance of the sensor 702 is derived from the sum of each of the individual capacitive layers. The sensor 702 is monitored by applying a voltage 718 across the two conductive electrodes 704 and 706. As a surface crack 702 forms and propagates in the host structure, the interdigitated conductive fingers of the conductive electrodes 704 and 706 and the dielectric material regions 708, 710, 712, 714, and 716 become damaged. The damage caused by the crack 720 decreases the overall capacitance of the sensor 702. In one embodiment, a length of the crack 720 is determined based on the deviation of the capacitance of the sensor 702 from the initial capacitance of each capacitor layer in the sensor 702. In the embodiment illustrated in FIGS. 7A and 7B, the sensor 702 is on a substrate 722 directly. In such a configuration, the substrate 722 is insulating, as in the resistive devices of FIGS. 1B and 1C.

Figure 7C:
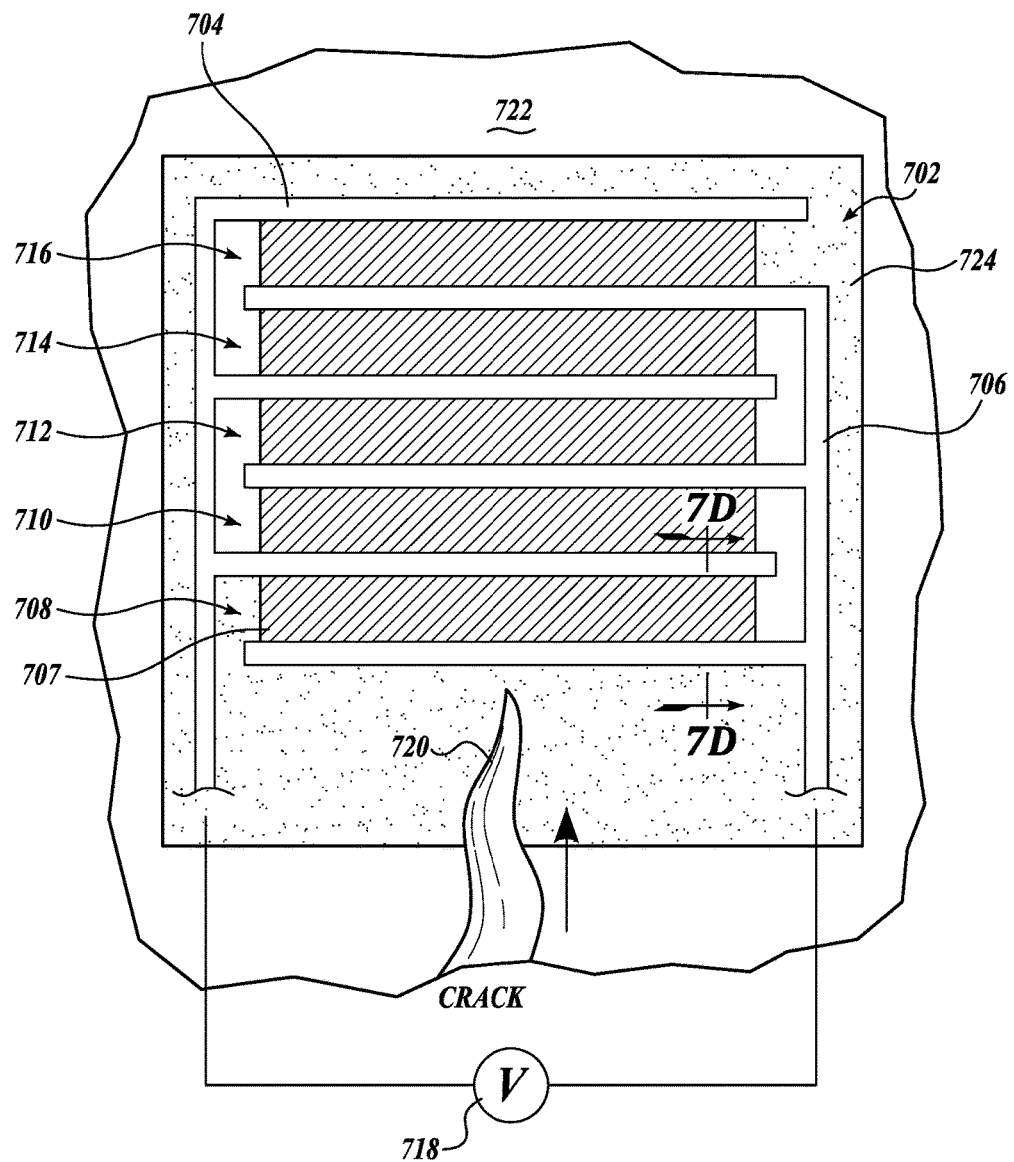
FIGS. 7C and 7D depict top and cross-sectional views, respectively, of an embodiment of a capacitance-based fuse-like sensor disposed on an insulating layer, in accordance with embodiments disclosed herein.
Figure 7D:
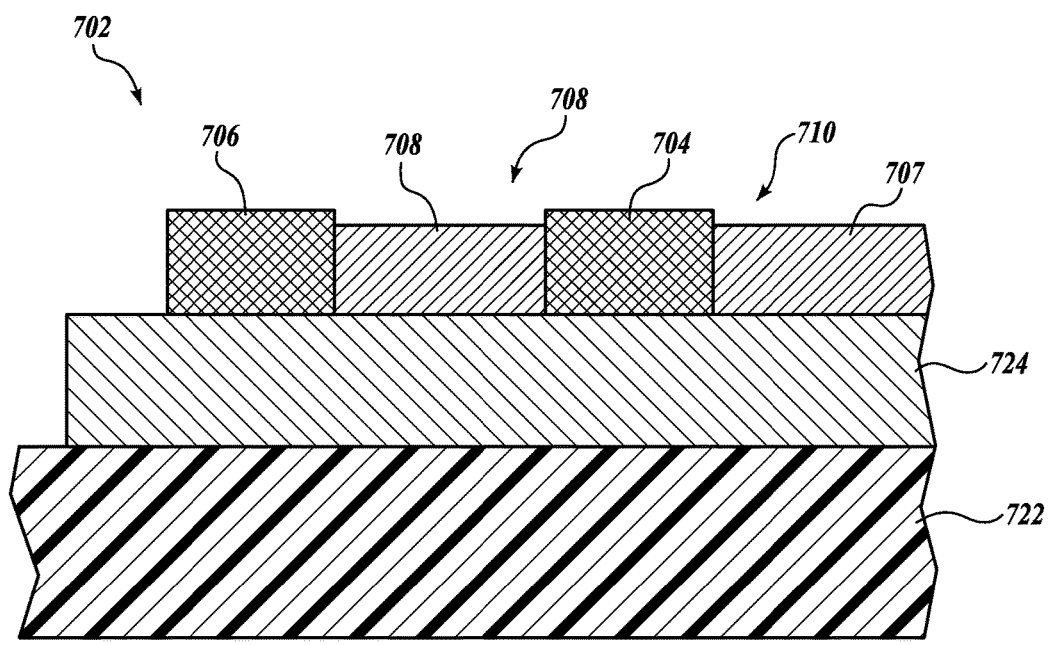

FIGS. 7C and 7D depict top and cross-sectional views, respectively, of an embodiment of a capacitance-based fuse-like sensor disposed on an insulating layer, in accordance with embodiments disclosed herein. FIG. 7C depicts an embodiment where the substrate 722 is electrically conductive. For the capacitor layers of sensor 702 to effectively work on conductive substrate 722, an insulation material 724 is first deposited on the substrate 722. The conductive electrodes 704 and 706 and the dielectric material 707 (in regions 708, 710, 712, 714, and 716) are then deposited on the insulation material 724. In one embodiment, to prevent a capacitive measurement between the conductive electrodes 704 and 706 via the substrate 722, the insulation material 724 is thicker than the dielectric material 708 between the conductive fingers of the conductive electrodes 704 and 706.

Figure 8A:
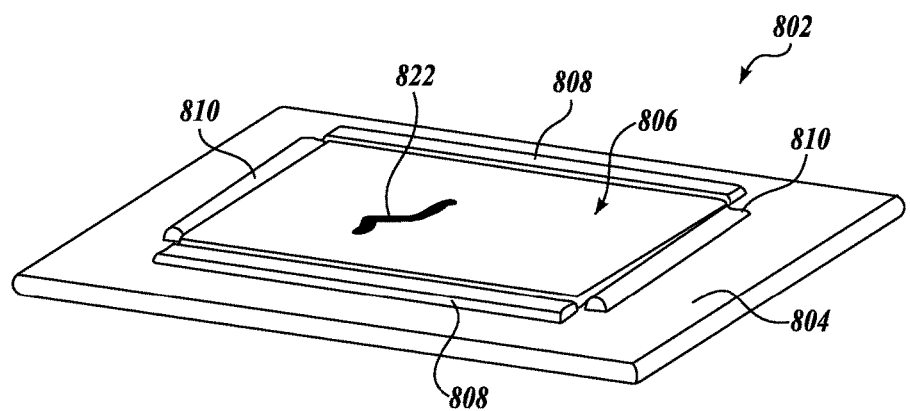
FIG. 8A depicts an example of a fuse-like matrix array sensor on a substrate, in accordance with embodiments disclosed herein.
Figure 8B:
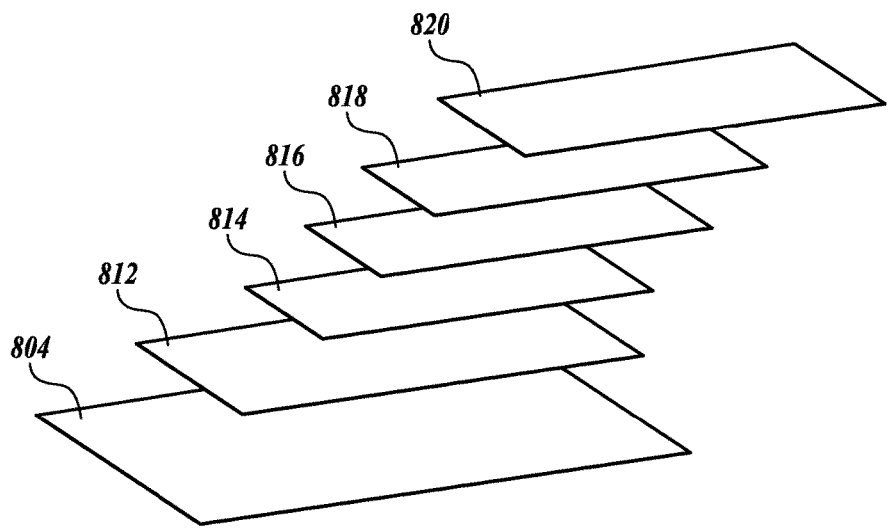
FIG. 8B depicts an embodiment of a multilayered fabrication of the fuse-like matrix array sensor shown in FIG. 8A, in accordance with embodiments disclosed herein.

The elevation view in FIG. 7D depicts an embodiment where the substrate 722 is electrically conductive. For the capacitor layers of sensor 702 to effectively work on conductive substrate 722, an insulation material 724 is first deposited on the substrate 722. The conductive electrodes 704 and 706 and the dielectric material 707 are then deposited on the insulation material 724. In one embodiment, to prevent a capacitive measurement between the conductive electrodes 704 and 706 via the substrate 722, the insulation material 724 is thicker than the dielectric material 708 between the conductive fingers of the conductive electrodes 704 and 706. Fuse-like sensors can be arranged in a capacitive/resistance matrix array. FIG. 8A depicts an example of a fuse-like matrix array sensor 802 on a substrate 804. In this embodiment, the sensor 802 includes a complex of interconnects 806, including conductive X lines 808 and Y lines 810 that form either a resistive or capacitive matrix array. FIG. 8B depicts an embodiment of a multilayered fabrication of the conductive X lines 808 and the Y lines 810, which is similar to multilayered fabrication used in touchscreen applications. In the embodiment shown in FIG. 8B, the multilayered fabrication includes a first dielectric layer 812, an X-layer 814 that forms the X lines 808, a second dielectric 816, a Y-layer 818 that forms Y lines 810, and an encapsulant 820 on the substrate 804. In one example, these layers can be printed on the substrate 804 in a DW process. In one embodiment, when traces in the X lines 808 and the Y lines 810 are damaged from the formation or propagation of a crack 822 (as shown in FIG. 8A), a length and/or a position of the crack 822 under the array sensor 802 is determined.

Figure 9:
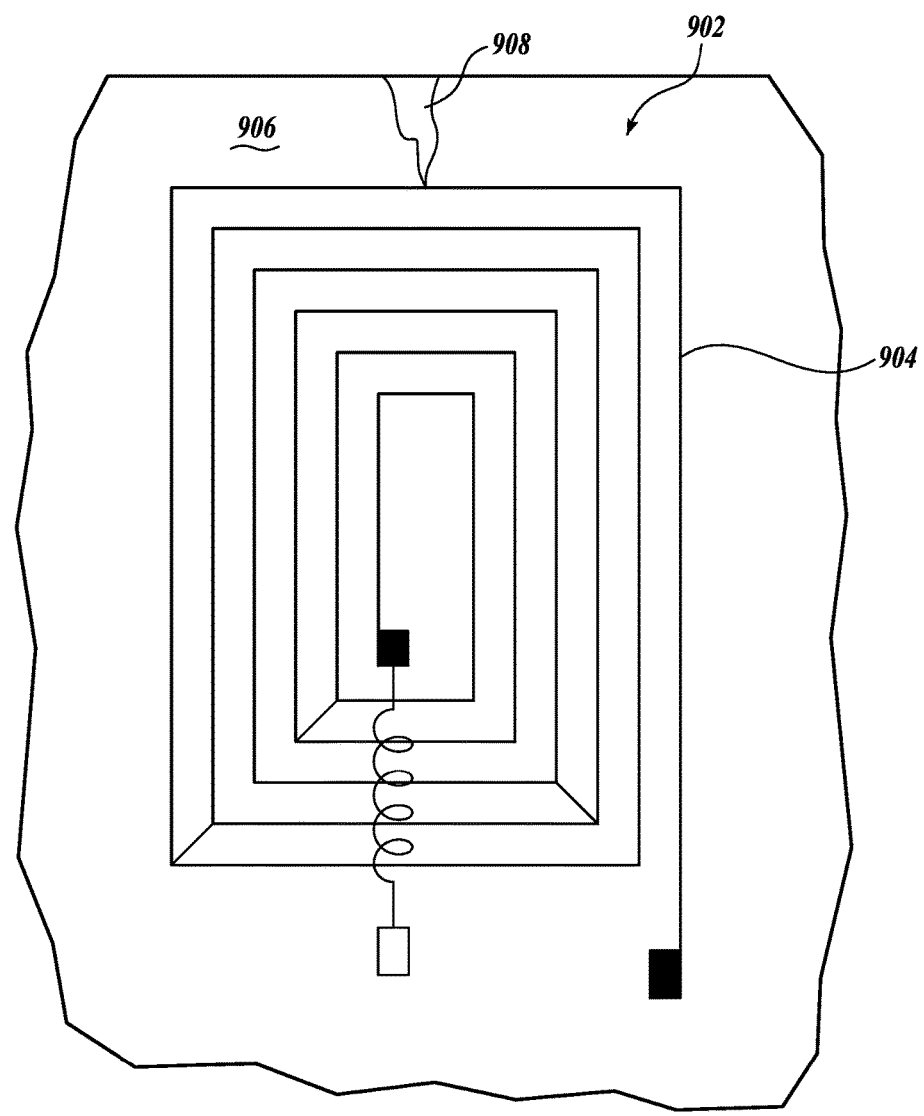
FIG. 9 depicts an embodiment of an antenna-based fuse-like sensor, in accordance with embodiments disclosed herein.

Another concept for fuse-like sensors is based on antenna principles. FIG. 9 depicts an embodiment of an antenna-based fuse-like sensor 902. In this example, the sensor 902 is formed from a multifaceted antenna coil 904 on a substrate 906. In one embodiment, the antenna coil 904 is printed on the substrate 906 using a DW process. As a crack 908 propagates through the substrate 906 under the printed features, the detectable frequencies of the antenna coil 904 will change. The change in detectable frequencies suggests the presence of the crack 908 and a length of the crack 908. In some embodiments, the substrate 906 is formed from non-conductive surfaces, such as composites, polymers, or some combination thereof. The ability to wirelessly detect frequencies from antenna coil 904 may reduce the need for certain hardware (e.g., connectors) in sensor 902 that could fail over time.

Figure 10A:
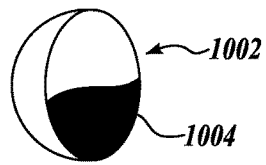
FIG. 10A depicts an embodiment of a filled capsule that contains a marker material, in accordance with embodiments disclosed herein.
Figure 10B:
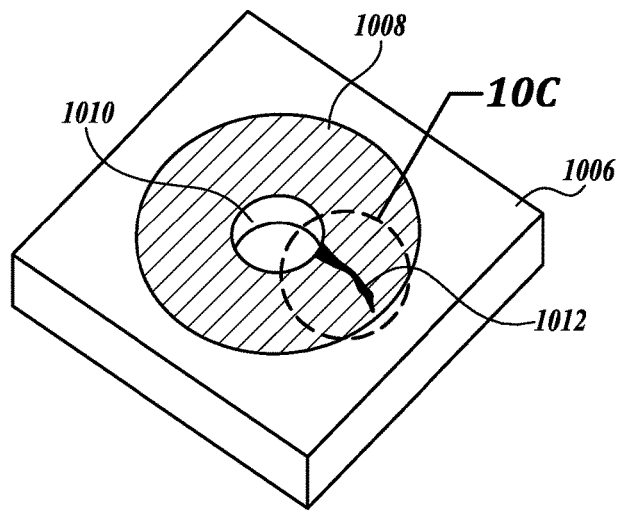
FIGS. 10B and 10C depict a perspective view and a detail view, respectively, of an embodiment of a substrate with a capsule region where filled capsules, such as the filled capsule shown in FIG. 10A, are adhered to a surface of the substrate, in accordance with embodiments disclosed herein.

Another concept for a fuse-like sensor is filled capsules on suspect surfaces. FIG. 10A depicts an embodiment of a filled capsule 1002 that contains a marker material 1004. In some embodiments, the filled capsule 1002 has an overall dimension (e.g., diameters) in a range from a nanometer to a micrometer. FIG. 10B depicts a substrate 1006 with a capsule region 1008.

Figure 10C:
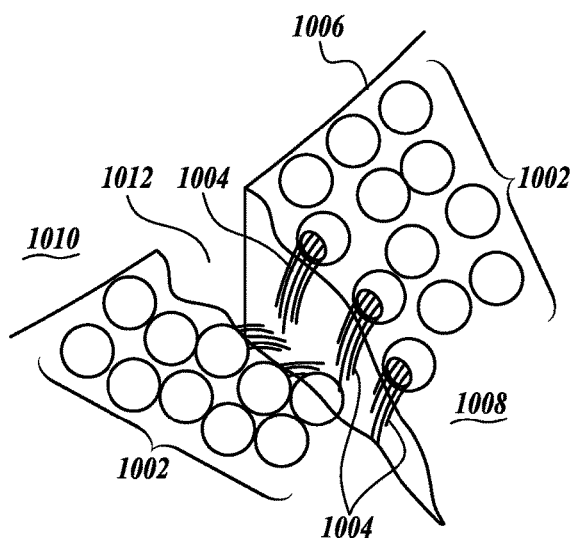

Filled capsules, such as the filled capsule 1002 depicted in FIG. 10A, are adhered to a surface of the substrate 1006 in the capsule region 1008. In one embodiment, the capsule region 1008 is an area where cracking or other deformations are likely to occur. In the example shown in FIG. 10B, the capsule region 1008 is around a hole 1010 in the substrate 1006. In some embodiments, the hole 1010 is a hole intended for a fastener, such as a rivet or a bolt. The filled capsules in the capsule region 1008 are adhered to the surface in such a way that one or more of the filled capsules will break open if a crack 1012 propagates through the substrate 1006 in the capsule region 1008. FIG. 10C depicts a detail view of the crack 1012 propagating in the substrate 1006. The capsule region 1008 includes filled capsules 1002. When the crack 1012 propagates through the substrate 1006, some of the filled capsules 1002 break open causing marker material 1004 to flow out of the filled capsules 1002.

In some embodiments, the marker material 1004 in the filled capsules 1002 is configured to enhance crack detection when released from the filled capsules 1002. In some embodiments, the marker material 1004 includes one or more of a material that produces a change in optical appearance (e.g., dye, coloring), a chemical (e.g., a chemical with a specific odor, outgassing elements), a material that produces a change in thermal characteristics (e.g., differing thermal conductivity), or a material that produces a change in electrical characteristics (e.g., magnetic, electrical conductivity). In another embodiment, the marker material 1004 in the filled capsules 1002 include two components that, when mixed together, change electrical, chemical, optical or magnetic properties of the sensor. The change in properties of the sensor can be detected to determine that a flaw (e.g., a crack) is in the substrate.

In another aspect, a system is provided. In one embodiment, the system includes:
  a substrate having a surface;
  a transferable medium; and
  a circuit including a plurality of conductive paths disposed adjacent the transferable medium, wherein the transferable medium is bonded to the surface of the substrate such that the circuit is configured to:
    detect an interruption or alteration of conduction of one or more of the plurality of conductive paths due to a flaw in the substrate, and
    identify the interrupted or altered one or more of the plurality of conductive paths based on one or more electrical characteristics of the circuit.

FIGS. 11A and 11B depict an embodiment of a circuit 1104 disposed directly on a transferable medium 1106 that is capable of being bonded to a substrate 1102, in accordance with any of the substrates and circuits described herein. The circuit 1104 includes conductive paths disposed directly on the transferable medium 1106 using any of the depositing methods described herein, such as DW, AJ, and the like. The transferable medium 1106 can take a number of forms, such as one or more B-stage epoxy films, one or more dissolving polymeric films, or any other kind of transferable medium.

In the embodiment shown in FIG. 11A, the circuit 1104 is disposed directly on the transferable medium 1106, but the transferable medium 1106 is not bonded to the substrate 1102. From that point, the transferable medium 1106 can be bonded to the substrate 1102, as shown in FIG. 11B. In some embodiments, the transferrable medium is bonded to the substrate using one or more of heat, pressure, one or more organic solvents, or ultraviolet light. In one embodiment, the transferable medium 1104 is bonded to a surface of the substrate 1102 such that the circuit 1104 is configured to detect an interruption or alteration of conduction of one or more of the plurality of conductive paths due to a flaw in the substrate and identify the interrupted or altered one or more of the plurality of conductive paths based on one or more electrical characteristics of the circuit 1104. In one example, the plurality of conductive paths are disposed directly on the transferable medium 1106 such that, when the transferable medium 1106 is bonded to the substrate 1102, the circuit 1104 is configured to monitor a plurality of conformal regions.

In addition to the devices described herein, other aspects include methods of utilizing these devices for structural health monitoring.

In one aspect, a method of producing a structural health monitoring crack detection system is provided. In one embodiment, the method includes:
  providing a substrate having a surface; and
  printing, by an aerosol jet method, conductive paths on the surface of the substrate, wherein the resistive traces are configured to break if a crack propagates through substrate under the conductive paths.

In another aspect, a method of monitoring the structural health of an object having a surface of interest is provided. In one embodiment, the method includes:
  providing a circuit adjacent the surface of the object, the circuit including a plurality of conductive paths disposed adjacent the surface of the object or on a transferable medium bonded to the surface of the substrate;
  obtaining an initial conductive state of the circuit; and
  monitoring an active conductive state of the circuit for deviations from the initial conductive state, wherein a deviation from the initial conductive state is indicative of an interrupted or alteration of conduction of at least one of the plurality of conductive paths.

While illustrative embodiments have been illustrated and described, it will be appreciated that various changes can be made therein without departing from the spirit and scope of the claimed subject matter.

The embodiments of the invention in which an exclusive property or privilege is claimed are defined as follows:

1. A sensor system for structural monitoring, comprising:
  a monolithic substrate having a continuous surface;
  a patterned insulating layer that is directly written as a plurality of lines disposed over the surface, wherein the plurality of lines is written by additive process only; and
  a circuit including a plurality of conductive paths that are directly written over the corresponding plurality of the lines of the patterned insulating layer of the substrate, wherein the plurality of conductive paths is written by additive process only, wherein as-written the conductive paths and the lines of the patterned insulating layer have the same width, wherein the surface is curved or stepped as a three-dimensional contour, wherein the plurality of conductive paths follow a continuous portion of the three-dimensional contour of the surface, and wherein the circuit is configured to:

detect an interruption or alteration of conduction of one or more of the plurality of conductive paths due to a flaw in the substrate, and identify the interrupted or altered one or more of the plurality of conductive paths based on one or more electrical characteristics of the circuit.

2. The system of claim 1, wherein each of the plurality of conductive paths is coupled to a first electrode and a second electrode, wherein the flaw in the substrate is a crack or strain beneath the interrupted or altered one or more of the plurality of conductive paths.

3. The system of claim 2, further comprising a single voltage or current source electrically coupled to the first electrode and the second electrode.

4. The system of claim 2, further comprising:

an additional conductive path not belonging to the plurality of conductive paths located between the first electrode and the second electrode, wherein, when conduction of the plurality of conductive paths is interrupted and conduction of the additional path is not interrupted, a resistance of the circuit is substantially the same as a resistance of the additional conductive path.

5. The system of claim 1, wherein at least two of the plurality of conductive paths include a resistor, and wherein the resistors have different resistance such that a total resistance of the circuit identifies the interrupted or altered one or more of the plurality of conductive paths.

6. The system of claim 1, wherein at least two of the plurality of conductive paths include a capacitor, and wherein the capacitors have different capacitance such that a total capacitance of the circuit identifies the interrupted or altered one or more of the plurality of conductive paths.

7. The system of claim 1, wherein each of the plurality of conductive paths includes a resistor or a capacitor arranged such that the one or more electrical characteristics of the circuit identify the interrupted or altered one or more of the plurality of conductive paths.

8. The system of claim 1, wherein the plurality of conductive paths form a multifaceted antenna coil, and wherein the one or more electrical characteristics of the circuit comprise a detectable frequency from the multifaceted antenna coil.

9. The system of claim 1, wherein the plurality of conductive paths comprise semi-conductive materials.

10. The system of claim 1, wherein the system is configured to determine a length of the flaw by identifying the interrupted or altered one or more of the plurality of conductive paths.

11. The system of claim 1, wherein the flaw comprises one or more of a surface crack, elastic deformation of the substrate, or plastic deformation of the substrate.

12. The system of claim 1, wherein at least a portion of the circuit is printed using a technique selected from the group consisting of aerosol jet direct writing, extrusion printing, ink-jet printing, screen printing, roll printing, gravure printing, and combinations thereof.

13. The system of claim 1, wherein the conductive paths are disposed directly on the surface of the substrate.

14. The system of claim 1, wherein the insulating layer is selected from the group consisting of a paint layer, a dielectric layer, a protective coating, and combinations thereof.

15. The system of claim 1, wherein the system is a structural health monitoring system configured to monitor an object that includes the substrate.

16. The system of claim 15, wherein the object is one or more of an aircraft component, a building component, a bridge component, or a pipeline component.

17. The system of claim 15, wherein the structural health monitoring system is configured to determine a life expectancy of the object based on data from the circuit.

18. A sensor system for structural monitoring, comprising:

a monolithic substrate having a continuous surface;

a patterned insulating layer that is directly written as a plurality of lines disposed over the surface, wherein the plurality of lines is written by additive process only;

a capacitive circuit including:

a first conductive electrode that is directly written over one line of the patterned insulating layer, wherein the first conductive electrode is written by additive process only, wherein as-written the first conductive electrode and the one line of the patterned insulating layer have the same width, a second conductive electrode that is directly written over another line of the patterned insulating layer, wherein the second conductive electrode is written by additive process only, wherein as-written the second conductive electrode and the another line of the patterned insulating layer have the same width, wherein the surface is curved or stepped as a three-dimensional contour, and wherein the first conductive electrode and the second conductive electrode follow a continuous portion of the three-dimensional contour of the surface, and a deposited dielectric material separating the first electrode and the second electrode, wherein the electrodes and the patterned insulating layer have the same width, wherein the circuit is configured to detect a change in a capacitance of the capacitive circuit due to a crack propagation in the substrate.

* * * * *